(12) United States Patent
Frost et al.

(10) Patent No.: US 7,488,754 B2
(45) Date of Patent: Feb. 10, 2009

(54) METHOD FOR THE TREATMENT OF POLYCYSTIC KIDNEY DISEASE

(75) Inventors: Philip Frost, Morris Township, NJ (US); Jeremy I. Levin, New City, NY (US)

(73) Assignee: Wyeth, Madison, NJ (US)

( * ) Notice: Subject to any disclaimer, the term of this patent is extended or adjusted under 35 U.S.C. 154(b) by 735 days.

(21) Appl. No.: 10/473,857

(22) PCT Filed: Apr. 5, 2002

(86) PCT No.: PCT/US02/10751

§ 371 (c)(1),
(2), (4) Date: Oct. 2, 2003

(87) PCT Pub. No.: WO02/083112

PCT Pub. Date: Oct. 24, 2002

(65) Prior Publication Data

US 2004/0063672 A1 Apr. 1, 2004

(51) Int. Cl.
*A61K 31/275* (2006.01)
*A61K 31/553* (2006.01)

(52) U.S. Cl. .................. 514/519; 514/211.05; 514/575

(58) Field of Classification Search ................. 514/519, 514/211.05
See application file for complete search history.

(56) References Cited

U.S. PATENT DOCUMENTS 6,002,008 A  12/1999  Wissner et al.
6,225,311 B1 *  5/2001  Levin et al. ............... 514/227.5
6,288,082 B1 *  9/2001  Wissner et al. ............ 514/313

FOREIGN PATENT DOCUMENTS

| WO | WO 00/44709 | 8/2000 |
| WO | WO 00/44710 | 8/2000 |
| WO | WO 00/44730 | 8/2000 |
| WO | WO 01/10827 | 2/2001 |

OTHER PUBLICATIONS

Levin et al., A novel inhibitor of tumor necrosis factor- (TNF-a) converting enzyme ameliorates polycystic kidney disease, Kidney Int. 2110 vol. 60(4):1240-1248.*
Singh et al. Environmental Health Perspectives, vol. 85. 361-370 (1990).*
Hoppe et al., Pharmacology Section, Sterling-Winthrop Research Institute, Rensselar, New York, 1955, 106-119.*
Freiberg et al. Antimicrobial Agents and Chemotherapy, 2707-2712, 2006.*
Obermüeller, Nicholas et al.: Amer. J. of Physiology (Mar. 2001) vol. 280, No. 3, pp. F540-F550.
Qian, Q. et al., Kidney International, (2001), 59/6, pp. 2005-2022.
Dell, K. M. et al., vol. 60, (2001), pp. 1240-1248.

* cited by examiner

*Primary Examiner*—Michael G Hartley
*Assistant Examiner*—Shirley V Gembeh
(74) *Attorney, Agent, or Firm*—David Rubin

(57) ABSTRACT

The present invention provides a method for treating, inhibiting the progression of, or eradicating polycystic kidney disease of in a patient in need thereof which comprises providing to said patient an effective amount of a TACE inhibitor compound alone or in combination with an effective amount of an EGF receptor kinase inhibitor.

11 Claims, No Drawings

METHOD FOR THE TREATMENT OF POLYCYSTIC KIDNEY DISEASE

FIELD OF INVENTION

The present invention relates to a method of treating polycystic kidney disease. More particularly it involves the use of tumor necrosis factors-alpha converting enzyme (TACE) inhibitor, alone or in combination with other agent(s) such as EGF receptor kinase inhibitor, to treat the disease.

BACKGROUND

Autosomal recessive polycystic kidney disease (ARPKD) is an inherited disorder that usually presents in the newborn period with massive kidney enlargement (due to rapidly expanding cysts) and hepaticfibrosis. ARPKD occurs in approximately 1:10,000 to 1:40,000 births and produces significant morbidity and mortality. Data from experimental models of both recessive and dominant forms of PKD have identified three key pathophysiologic processes in cyst formation and enlargement: increased cell proliferation, increased fluid secretion and altered matrix biology. (Marcia N S, Sweeny W E Armer E D: New insights into the molecular pathophyscology of polycystic kidney disease, *Kidney Int*, 55:1187-1197, 1999). A growing body of evidence has established the central role of the epidermal growth factor receptor (EGFR) in the pathogenesis of cell proliferation in PKD.

Published reports have also suggested that transforming growth factor-α (TGF-α) a ligand of the EGFR, is abnormally expressed in PKD. Mice transgenic for TGF-α develop renal cysts. TGF-α is present in mitogenic quantities in cyst fluid from bpk mice (a murine model of ARPKD) and immunoprecipitation of TGF-α reduces this mitogenic effect (Abstract; *J Am Soc Nephrol* 7:1610, 1996).

U.S. Pat. No. 6,002,008 discloses that certain EGF receptor kinase inhibitors are useful in the treatment of PKD; however no disclosure of the present invention is disclosed therein.

There is currently no completely effective therapy for polycystic kidney disease. A search for therapeutic agents useful for the treatment of PKD is ongoing.

SUMMARY OF INVENTION

The present invention provides a method for treating, inhibiting the progression of, or eradicating polycystic kidney disease of in a patient in need thereof which comprises providing to said patient an effective amount of a TACE inhibitor compound alone or in combination with an effective amount of an EGF receptor kinase inhibitor.

DETAILED DESCRIPTION OF THE PREFERRED EMBODIMENTS

Preferred TACE inhibitor compounds are described in WO 00/44730 and corresponding U.S. Pat. No. 6,544,984, WO 00/44749 and corresponding U.S. Pat. No. 6,946,473, WO 00/44709 and corresponding U.S. Pat. Nos. 6,225,311, 6,716,833 (including related publications US2003-0212049A1, US2003-0008849A1 and US2005-0113345A1) and U.S. Pat. No. 6,812,227 (including related publication US2004-0033988A1), WO 00/44711 and corresponding U.S. Pat. No. 6,326,516, WO 00/44710 and corresponding U.S. Pat. Nos. 6,277,885 and 6,762,178, WO 00/44716 and corresponding U.S. Pat. No. 6,313,123, WO 00/44740 and corresponding U.S. Pat. No. 6,200,996 (including related publication US2002-0188132A1), WO 00/44713 and corresponding U.S. Pat. Nos. 6,340,691 and 6,825,354 (including related publication US2002-0147342A1), and WO 00/44723 and corresponding U.S. Pat. Nos. 6,358,980 and 6,753,337 (including related publication US2002-0086890A1), and publication US2004-0229924A1, each of which is hereby incorporated by reference thereto.

Especially preferred TACE inhibitor compounds include those of formula I:

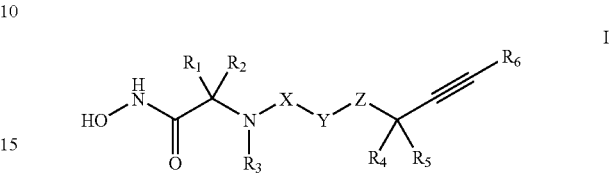

wherein:
X is $SO_2$ or $—P(O)—R_{10}$;
Y is aryl or heteroaryl, with the proviso that X and Z may not be bonded to adjacent atoms of Y;
Z is O, NH, $CH_2$ or S;
$R_1$ is hydrogen, aryl, alkyl of 1-6 carbon atoms, alkenyl of 2-6 carbon atoms, alkynyl of 2-6 carbon atoms;
$R_2$ is hydrogen, aryl, aralkyl, heteroaryl, heteroaralkyl, cycloalkyl of 3-6 carbon atoms, $C_4$-$C_8$ cycloheteroalkyl, alkyl of 1-6 carbon atoms, alkenyl of 2-6 carbon atoms, alkynyl of 2-6 carbon atoms;
or $R_1$ and $R_2$, together with the atom to which they are attached, may form a ring wherein $R_1$ and $R_2$ represent a divalent moiety of the formula:

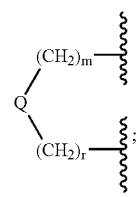

wherein
Q=a carbon-carbon single or double bond, O, S, SO, $SO_2$, $—N—R_{11}$, or $—CONR_{14}$;
m=1-3;
r=1 or 2, with the proviso that when Q is a bond, r is equal to 2;
$R_3$ is hydrogen, alkyl of 1-6 carbon atoms, cycloalkyl of 3-6 carbon atoms, C4-C8 cycloheteroalkyl, aralkyl, or heteroaralkyl;
or $R_1$ and $R_3$, together with the atoms to which they are attached, may form a 5 to 8 membered ring wherein $R_1$ and $R_3$ represent divalent moieties of the formulae:

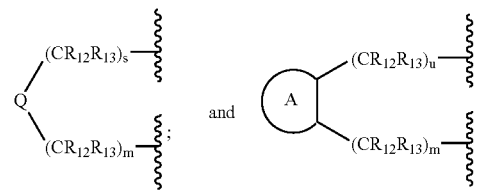

wherein Q and m are as defined above;

A is aryl or heteroaryl;

s is 0-3;

u is 14;

$R_4$ and $R_5$ are each, independently, hydrogen or alkyl of 1-6 carbon atoms, —CN, or —CCH;

$R_6$ is hydrogen, aryl, heteroaryl, alkyl of 1-6 carbon atoms, alkenyl of 2-6 carbon atoms, alkynyl of 2-6 carbon atoms, cycloalkyl of 3-6 carbon atoms, or —$C_5$-$C_8$-cycloheteroalkyl;

$R_8$ and $R_9$ are each, independently, hydrogen, alkyl of 1-6 carbon atoms, alkenyl of 2-6 carbon atoms, alkynyl of 2-6 carbon atoms, cycloalkyl of 3-6 carbon atoms, aryl, aralkyl, heteroaryl, heteroaralkyl, or —$C_4$-$C_8$-cycloheteroalkyl;

$R_{10}$ is alkyl of 1-6 carbon atoms, cycloalkyl of 3-6 carbon atoms, aryl or heteroaryl;

$R_{11}$ is hydrogen, alkyl of 1-6 carbon atoms, cycloalkyl of 3-6 carbon atoms, aryl, heteroaryl, —$S(O)_nR_8$, —$COOR_8$, —$CONR_8R_9$, —$SO_2NR_8R_9$ or —$COR_8$;

$R_{12}$ and $R_{13}$ are independently selected from H, —$OR_8$, —$NR_8R_9$, alkyl of 1-6 carbon atoms, alkenyl of 2-6 carbon atoms, alkynyl of 2-6 carbon atoms, cycloalkyl of 3-6 carbon atoms, aryl, heteroaryl, —$COOR_8$, —$CONR_8R_9$; or $R_{12}$ and $R_{13}$ together form a —$C_3$-$C_6$-cycloalkyl of 3-6 carbon atoms or a —$C_5$-$C_8$-cycloheteroalkyl ring; or $R_{12}$ and $R_{13}$, together with the carbon to which they are attached, form a carbonyl group;

with the proviso that $R_{10}$ and $R_{12}$ or $R_{11}$ and $R_{12}$ may form a cycloheteroalkyl ring when they are attached to adjacent atoms;

$R_{14}$ is hydrogen, aryl, heteroaryl, alkyl of 1-6 carbon atoms or cycloalkyl of 3-6 carbon atoms;

and n is 0-2;

or a pharmaceutically acceptable salt thereof.

Heteroaryl, as used throughout, is a 5-10 membered mono- or bicyclic ring having from 1-3 heteroatoms selected from N, $NR_{14}$, S and O. Heteroaryl is preferably wherein K is O, S or —NR14 and R14 is hydrogen, aryl, heteroaryl, alkyl of 1-6 carbon atoms, or cycloalkyl of 3-6 carbon atoms. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. Heteroaryl groups may optionally be mono or di substituted.

C4-C8 cycloheteroalkyl as used herein refers to a 5 to 9 membered saturated or unsaturated mono or bi-cyclic ring having 1 or 2 heteroatoms selected from N, $NR_{14}$, S or O. Heterocycloalkyl rings of the present invention are preferably selected from;

wherein K is $NR_{14}$, O or S and $R_{14}$ is a bond, hydrogen, aryl, heteroaryl, alkyl of 1-6 carbon atoms, or cycloalkyl of 3-6 carbon atoms.

Preferred heterocycloalkyl rings include piperidine, piperazine, morpholine, tetrahydropyran, tetrahydrofuran or pyrrolidine.

Cycloheteroalkyl groups of the present invention may optionally be mono- or di-substituted.

Aryl, as used herein refers to a phenyl or napthyl rings which may, optionally be mono-, di- or tri-substituted.

Alkyl, alkenyl, alkynyl, and perfluoroalkyl include both straight chain as well as branched moieties. Alkyl, alkenyl, alkynyl, and cycloalkyl groups may be unsubstituted (carbons bonded to hydrogen, or other carbons in the chain or ring) or may be mono- or poly-substituted. Lower alkyl moieties contain from 1 to 6 carbon atoms.

Aralkyl as used herein refers to a substituted alkyl group, -alkyl-aryl, wherein alkyl is lower alkyl and preferably from 1 to 3 carbon atoms, and aryl is as previously defined.

Heteroaralkyl as used herein refers to a substituted alkyl group, alkyl-heteroaryl wherein alkyl is lower alkyl and preferably from 1 to 3 carbon atoms, and heteroaryl is as previously defined.

Halogen means bromine, chlorine, fluorine, and iodine.

Suitable substituents of aryl, aralkyl, heteroaryl, heteroaralkyl, alkyl, alkenyl, alkynyl, and cycloalkyl include, but are not limited to hydrogen, halogen, alkyl of 1-6 carbon atoms; alkenyl of 2-6 carbon atoms; alkynyl of 2-6 carbon atoms, cycloalkyl of 3-6 carbon atoms, —$OR_8$, —$[O(CH_2)_p]_q$—$OCH3$, CN, —$COR_8$, perfluoroalkyl of 1-4 carbon atoms, —O-perfluoroalkyl of 1-4 carbon atoms, —CONR$_8$R$_9$, —S(O)$_n$R$_8$, —S(O)$_n$R$_{18}$C(O)OR$_8$, —S(O)$_n$R$_{18}$OR$_9$, —S(O)$_n$R$_{18}$NR$_8$R$_9$, —S(O)$_n$R$_{18}$NR$_8$R$_9$COOR$_8$, —S(O)$_n$R$_{18}$NR$_8$COR$_9$, —OPO(OR$_8$)OR$_9$, —PO(OR$_8$)R$_9$, —OC(O)NR$_8$R$_9$, —C(O)NR$_8$OR$_9$, —C(O)R$_{18}$NR$_8$R$_9$, —COOR$_8$, —SO$_3$H, —NR$_8$R$_9$, —N[(CH$_2$)$_2$]$_2$NR$_8$, —NR$_8$COR$_9$, —NR$_8$C(O)CH=CHaryl, —NR$_8$C(O)(CH$_2$)$_n$NR$_8$R$_9$, —NR$_8$C(O)CH$_2$NHCH$_2$aryl, NR$_8$C(O)R$_{18}$, —NR$_8$COOR$_9$, —SO$_2$NR$_8$R$_9$, —NO$_2$, —N(R$_8$)SO$_2$R$_9$, —NR$_8$CONR$_8$R$_9$, —NR$_8$C(=NR$_9$)NR$_8$R$_9$, —NR$_8$C(=NR$_9$)N(SO2R$_8$)R$_9$, NR$_8$C(=NR$_9$)N(C=OR$_8$)R$_9$-tetrazol-5-yl, —SO$_2$NHCN, —SO$_2$NHCONR$_8$R$_9$, —(OR18)NR$_8$S(O)R$_9$, —(OR$_{18}$)NR$_8$C(O)R$_9$, —(OR$_{18}$)NR$_8$C(O)NR$_8$R$_9$, —(OR18)NR$_8$COOR$_9$, —(OR$_{18}$)NR$_8$R$_9$, phenyl, heteroaryl, or —C$_4$-C$_8$-cycloheteroalkyl;

wherein —NR$_8$R$_9$ may form a heterocyclic group as previously defined, such as pyrrolidine, piperidine, morpholine, thiomorpholine, oxazolidine, thiazolidine, pyrazolidine, piperazine, and azetidine ring; p is 1 or 2, q is 1 through 3 and R$_{18}$ is alkyl of 1-20 carbon atoms.

In some preferred embodiments of the present invention R$_8$ and R$_{18}$ may be further substituted with halogen, C$_1$-C$_3$ alkyl, C$_1$-C$_3$ alkoxy and OH, and NO$_2$.

When a moiety contains more than substituent with the same designation (i.e., phenyl tri-substituted with R.) each of those substituents (R$_1$ in this case) may be the same or different.

Especially preferred TACE inhibitor compounds of the present invention include compounds of formula II, III and IV:

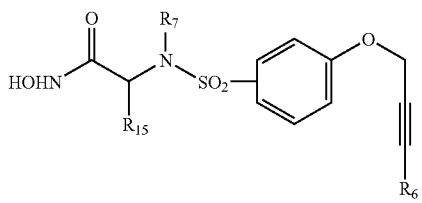

(II)

wherein

R$_6$ is as defined above with CH$_3$ and CH$_2$OH being preferred; R$_7$ is H or alkyl with H or methyl being preferred; and R$_{15}$ is alkyl, with isopropyl and CH(CH$_3$)OH being preferred.

(III)

wherein R$_6$ is defined as above with methyl and CH$_2$OH being preferred;

R$_{16}$ and R$_{17}$ are alkyl preferably methyl.

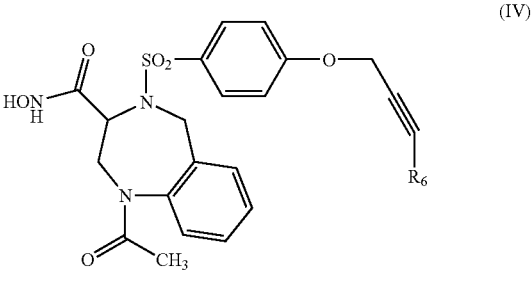

(IV)

wherein R$_6$ is as defined above with methyl being preferred.

TACE inhibitor compounds which are especially useful in the present invention are 4-(4-but-2-ynyloxy-benzenesulfonyl)-2,2-dimethyl-thiomorpholine-3-carboxylic acid hydroxyamide; (3S)-N-hydroxy-4-({4-[(4-hydroxy-2-butynyl)oxy]phenyl}sulfonyl)-2,2-dimethyl-3-thiomorpholinecarboxamide; (2R)-N-hydroxy-2-[({4-[(4-hydroxy-2-butynyl)oxy]phenyl}sulfonyl)(methyl)amino]-3-methylbutanamide; and (2R,3S)-2-({[4-(2-butynyloxy)phenyl]sulfonyl}amino)-N,3-dihydroxybutanamide.

The present invention also encompasses a method for the treatment of PKD by using a TACE inhibitors compound in combination with an EGF receptor kinase inhibitor.

Preferred EGF receptor kinase inhibitor compounds are described in U.S. Pat. No. 6,002,008 which is hereby incorporated by reference thereto. The compound 4-dimethylamineo-but-2-enoic acid [4-(3-chloro-4-fluoro-phenylamino)-3-cyano-7-ethoxy-quinolin-6-yl]-amide is especially preferred.

Preferred TACE inhibitor compounds of the present invention are described in WO 00/44730, WO 00/44749, WO 00/44709, WO 00/44711, WO 00/44710, WO 00/44716, WO 00/44740, WO 00/44713, and WO 00/44723. For example the following compounds are preferred compounds in the present invention: 4-(4-substituted-benzenesulfonyl)-2,3,4,5-tetrahydro-1H-[1,4]benzodiazepine-3-hydroxamic acids such as 1-Acetyl-4-(4-but-2-ynyloxy-benzenesulfonyl)-2,3,4,5-tetrahydro-1H-[1,4]benzodiazepine-3-carboxylic acid, hydroxyamide;

4-(4-But-2-ynyloxy-benzene-sulfonyl)-1-(2-thienylcarbonyl)-2,3,4,5-tetrahydro-1H-[1,4]benzodiazepine-3-carboxylic acid, hydroxyamide;

1-Benzoyl-4-(4-but-2-ynyloxybenzenesulfonyl)-2,3,4,5-tetrahydro-1H-[1,4]benzodiazepine-3-carboxylic acid, hydroxyamide;

4-(4-But-2-ynyloxybenzene-sulfonyl)-1-(2-furanylcarbonyl)-2,3,4,5-tetrahydro-1 H-[1,4]benzodiazepine-3-carboxylic acid, hydroxyamide;

4-(4-But-2-ynyloxybenzene-sulfonyl)-1-(methanesulfonyl)-2,3,4,5-tetrahydro-1H-[1,4]benzodiazepine-3-carboxylic acid, hydroxyamide;

4-(4-But-2-ynyloxybenzene-sulfonyl)-1-methoxyacetyl-2,3,4,5-tetrahydro-1H-[1,4]benzodiazepine-3-carboxylic acid, hydroxyamide;

4-(4-But-2-ynyloxybenzene-sulfonyl)-1-(3-pyridinylcarbonyl)-2,3,4,5-tetrahydro-1H-[1,4]benzodiazepine-3-carboxylic acid, hydroxyamide;

4-(4-But-2-ynyloxybenzene-sulfonyl)-1-(4-pyridinylcarbonyl)-2,3,4,5-tetrahydro-1H-[1,4]benzodiazepine-3-carboxylic acid, hydroxyamide;

1-Benzoyl-4-(4-[4-methoxybut-2-ynyloxy]benzenesulfonyl)-2,3,4,5-tetrahydro-1H-[1,4]benzodiazepine-3-carboxylic acid, hydroxyamide;
4-(4-[4-Methoxybut-2-ynyloxy]benzenesulfonyl)-1-(3-pyridinylcarbonyl)-2,3,4,5-tetrahydro-1H-[1,4]benzodiazepine-3-carboxylic acid, hydroxyamide;
4-(4-Pent-2-ynyloxy-benzene-sulfonyl)-1-(3-pyridinylcarbonyl)-2,3,4,5-tetrahydro-1H-[1,4]benzodiazepine-3-carboxylic acid, hydroxyamide;
4-(4-[4-Hydroxybut-2-ynyloxy]benzenesulfonyl)-1-(4-pyridinylcarbonyl)-2,3,4,5-tetrahydro-1H-[1,4]benzo-diazepine-3-carboxylic acid, hydroxyamide;
4-(4-[4-Methoxybut-2-ynyloxy]-benzenesulfonyl)-1-(2-thienylcarbonyl)-2,3,4,5-tetrahydro-1H-[1,4]benzodiazepine-3-carboxylic acid, hydroxyamide;
1-(Benzoyl)-4-(4-pent-2-ynyloxy-benzenesulfonyl)-2,3,4,5-tetrahydro-1H-[1,4]benzodiazepine-3-carboxylic acid, hydroxyamide;
1-Propionyl-4-(4-[4-hydroxybut-2-ynyloxy]benzenesulfonyl)-2,3,4,5-tetrahydro-1H-[1,4]benzodiazepine-3-carboxylic acid, hydroxyamide;
1-(N,N-Dimethylaminoacetyl)-4-(4-[4-methoxybut-2-ynyloxy]benzenesulfonyl)-2,3,4,5-tetrahydro-1H-[1,4 ]benzodiazepine-3-carboxylic acid, hydroxyamide;
1-(Acetylaminoacetyl)-4-(4-but-2-ynyloxybenzenesulfonyl)-2,3,4,5-tetrahydro-1H-[1,4]benzodiazepine-3-carboxyiic acid, hydroxyamide;
1-(Ethoxyacetyl)-4-(4-[4-methoxybut-2-ynyloxy]benzenesulfonyl)-2,3,4,5-tetrahydro-1H-[1,4]benzodiazepine-3-carboxylic acid, hydroxyamide;
4-(4-But-2-ynyloxybenzenesulfonyl)-1-(3-thienylcarbonyl)-2,3,4,5-tetrahydro-1H-[1,4]benzodiazepine-3-carboxylic acid, hydroxyamide;
1-(Ethoxyacetyl)-4-(4-[4-ethoxybut-2-ynyloxy]benzenesulfonyl)-2,3,4,5-tetrahydro-1H-[1,4]benzodiazepine-3-carboxylic acid, hydroxyamide;
1-(Acetylaminoacetyl)-4-(4-[4-methoxybut-2-ynyloxy]benzenesulfonyl)-2,3,4,5-tetrahydro-1H-[1,4]benzodiazepine-3-carboxylic acid, hydroxyamide;
1-(Cyclopropylcarbonyl)-4-(4-[4-methxybut-2-ynyloxy]benzenesulfonyl)-2,3,4,5-tetrahydro-1H-[1,4]benzodiazepine-3-carboxylic acid, hydroxyamide;
1-(Cyclobutylcarbonyl)-4-(4-but-2-ynyloxybenzeneulfonyl)-2,3,4,5-tetrahydro-1H-[1,4]benzodiazepine-3-carboxylic acid, hydroxyamide;
4-(4-But-2-ynyloxybenzene-sulfonyl)-1-(propionyl)-2,3,4,5-tetrahydro-1H-[1,4]benzodiazepine-3-carboxylic acid, hydroxyamide;
4-(4-[4-Methoxybut-2-ynyloxy]benzenesulfonyl)-1-(3-methyl-2-thienylcarbonyl)-2,3,4,5-tetrahydro-1H-[1,4]benzodiazepine-3-carboxylic acid, hydroxyamide;
4-(4-But-2-ynyloxybenzene-sulfonyl)-1-(3-methoxypropionyl)-2,3,4,5-tetrahydro-1H-[1,4]benzodiazepine-3-carboxylic acid, hydroxyamide;
4-(4-But-2-ynyloxybenzene-sulfonyl)-1-(2-chlorobenzoyl)-2,3,4,5-tetrahydro-1H-[1,4]benzodiazepine-3-carboxylic acid, hydroxyamide;
4-(4-But-2-ynyloxybenzene-sulfonyl)-1-(2-fluorobenzoyl)-2,3,4,5-tetrahydro-1H-[1,4]benzodiazepine-3-carboxylic acid, hydroxyamide;
4-(4-But-2-ynyloxybenzene-sulfonyl)-1-(4-methyl-2-furanylcarbonyl)-2,3,4,5-tetrahydro-1H-[1,4]benzodiazepine-3-carboxylic acid, hydroxyamide;
4-(4-But-2-ynyloxybenzene-sulfonyl)-1-(3-furanylcarbonyl)-2,3,4,5-tetrahydro-1H-[1,4]benzodiazepine-3-carboxylic acid, hydroxyamide;
4-(4-But-2-ynyloxybenzene-sulfonyl)-1-(phenoxyacetyl)-2,3,4,5-tetrahydro-1H-[1,4]benzodiazepine-3-carboxylic acid, hydroxyamide;
4-(4-But-2-ynyloxybenzene-sulfonyl)-1-[2-(1-pyrazolyl)phenylcarbonyl]-7-methyl-2,3,4,5-tetrahydro-1H-[1,4]-benzodiazepene-3-carboxylic acid, hydroxyamide;
4-(4-But-2-ynyloxybenzene-sulfonyl)-1-(5-chloro-2-thienylcarbonyl)-2,3,4,5-tetrahydro-1H-[1,4]benzodiazepine-3-carboxylic acid, hydroxyarmide;
4-(4-But-2-ynyloxybenzene-sulfonyl)-1-(5-chloro-2-furanylcarbonyl)-2,3,4,5-tetrahydro-1H-[1,4]benzodiazepine-3-carboxylic acid, hydroxyamide;
4-(4-[4-Methoxybut-2-ynyloxy]-benzenesulfonyl)-1-propionyl-2,3,4,5-tetrahydro-1H-[1,4]benzodiazepine-3-carboxylic acid, hydroxyamide;
4-(4-[4-Methoxybut-2-ynyloxy]benzenesulfonyl)-1-(3-thienylcarbonyl)-2,3,4,5-tetrahydro-1H-[1,4]benzo-diazepine-3-carboxylic acid, hydroxyamide;
1-(Aminoacetyl)-4-(4-but-2-ynyloxybenzenesulfonyl)-2,3,4,5-tetrahydro-1H-[1,4]benzodiazepine-3-carboxylic acid, hydroxyamide;
1-Hexanoyl-4-(4-[4-methoxybut-2-ynyloxy]benzenesulfonyl)-2,3,4,5-tetrahydro-1H-[1,4]benzodiazepine-3-carboxylic acid, hydroxyamide;
4-(4-But-2-ynyloxy-benzenesulfonyl)-1-(N,N-Dimethylaminoacetyl)-2,3,4,5-tetrahydro-1H-[1,4]benzodiazepine-3-carboxylic acid, hydroxyamide;
4-(4-But-2-ynyloxybenzene-sulfonyl)-1-(cyclopropylcarbonyl)-2,3,4,5-tetrahydro-1H-[1,4]benzodiazepine-3-carboxylic acid, hydroxyamide;
4-(4-But-2-ynyloxybenzenesulfonyl)-1-(cycloyhexylcarbonyl)-2,3,4,5-tetrahydro-1H-[1,4]-benzodiazepine-3-carboxylic acid, hydroxyamide;
1-Methoxyacetyl-4-(4-[4-methoxybut-2-ynyloxy]benzenesulfonyl)-7-methyl-2,3,4,5-tetrahydro-1H-[1,4]-benzodiazepine-3-carboxylic acid, hydroxyamide;
1-Benzoyl-4-(4-but-2-ynyloxybenzenesulfonyl)-7-methyl-2,3,4,5-tetrahydro-1H-[1,4]-benzodiazepine-3-carboxylic acid, hydroxyamide;
1-(Benzoyl)-4-(4-but-2-ynyloxybenzenesulfonyl)-8-chloro-2,3,4,5-tetrahydro-1H-[1,4]benzodiazepine-3-carboxylic acid, hydroxyamide; and
1-Acetyl-4-{[4-(2-butynyloxy)phenyl]sulfonyl}-7-fluoro-N-hydroxy-2,3,4,5-tetrahydro-1H-1,4-benzodiazepine-3-carboxamide.

Other preferred TACE inhibitor compounds include acetylenic ortho-sulfonamido and phosphinic acid amido bicyclic heteroaryl hydroxamic acids such as 4-[(4-But-2-ynyloxy-benzenesulfonyl)-methyl-amino]-1,3-dimethyl-1H-pyrazolo[3,4-b]pyridine-5-carboxylic acid hydroxyamide;
4-[(4-But-2-ynyloxy-benzenesulfonyl)-methyl-amino]-3-methyl-isoxazolo-[5,4-b]pyridine-5-carboxylic acid hydroxyamide;
4-[(4-But-2-ynyloxy-benzenesulfonyl)-methyl-amino]-8-methoxy-quinoline-3-carboxylic acid hydroxyamide;
4-[(4-But-2-ynyloxy-benzenesulfonyl)-methyl-amino]-3-methyl-isothiazolo-[5,4-b]pyridine-5-carboxylic acid hydroxyamide; and
8-Bromo-4-[{[4-(2-butynyloxy)phenyl]sulfonyl}(methyl)amino]-N-hydroxy-3-quinolinecarboxamide.

Still other preferred TACE inhibitor compounds include aryl sulfonamide hydroxamic acid MMP/TACE inhibitors in which the sulfonyl aryl group is para-substituted with a substituted butynyl moiety or a propargylic ether, amine or sulfide such as 2-[(4-But-2-ynyloxy-benzenesulfonyl)-methyl-amino]-N-hydroxy-3-methyl-butyramide;
2-[(4-But-2-ynyloxy-benzenesulfonyl)-methyl-amino]-N-hydroxy-acetamide N-Hydroxy-2-[(4-methoxy-benzenesulfonyl)-methyl-amino]-3-methyl-butyramide;
2-[(4-But-2-ynyloxy-benzenesulfonyl)-pyridin-3-ylmethyl-amino]-N-hydroxy-acetamide hydrochloride;
2-(4-But-2-ynyloxy-benzenesulfonylamino)-N-hydroxy-acetamide;
2-(4-But-2-ynyloxy-benzenesulfonylamino)-N-hydroxy-3-methyl-butyramide;
2-(4-But-2-ynyloxy-benzenesulfonylamino)-N-hydroxy-propionamide;
2-[(4-But-2-ynyloxy-benzenesulfonyl)-pyridin-3-ylmethyl-amino]-N-hydroxy-propionamide hydrochloride;
2-(4-But-2-ynyloxy-benzenesulfonylamino)-N-hydroxy-2-methyl-propionamide;
4-(4-But-2-ynyloxy-benzenesulfonyl)-2,2-dimethyl-thiomorpholine-3-carboxylic acid hydroxyamide;
4-(4-Hept-2-ynyloxy-benzenesulfonyl)-2,2-dimethyl-thiomorpholine-3-carboxylic acid hydroxyamide;
2-(4-But-2-ynyloxy-benzenesulfonyl)-1,2,3,4-tetrahydro-isoquinoline-3-carboxylic acid hydroxyamide;
4-Benzoyl-1-(4-but-2-ynyloxy-benzenesulfonyl)-[1,4]diazepane-2-carboxylic acid hydroxyamide;
1-(4-But-2-ynyloxy-benzenesulfonyl)-4-methyl-piperazine-2-carboxylic acid hydroxyamide hydrochloride;
4-[4-(4-Hydroxy-but-2-ynyloxy)-benzenesulfonyl]-2,2-dimethyl-thiomorpholine-3-carboxylic acid hydroxyamide;
4-[4-But-2-ynyloxy-benzenesulfonyl]-3-hydroxycarbamoyl-piperazine-1-carboxylic acid tert-butyl ester;
2-(4-But-2-ynyloxy-benzenesulfonylamino)-N-hydroxy-2-methylpropionamide;
2-(4-But-2-ynyloxy-benzenesulfonylamino)-5-guanidino-pentanoic acid hydroxyamide;
2-(4-But-2-ynyloxy-benzenesulfonylamino)-5-(4-methyl-benzenesulfonyl-guanidino)-pentanoic acid hydroxyamide;
3-(4-But-2-ynyloxy-benzenesulfonylamino)-N-hydroxy-succinamic acid cyclohexyl ester;
2-(4-But-2-ynyloxy-benzenesulfonylamino)-3-cyclohexyl-N-hydroxy-propionamide;
2-(4-But-2-ynyloxy-benzenesulfonylamino)-2-cyclohexyl-N-hydroxy-acetamide
3-tert-Butylsulfanyl-2-(4-but-2-ynyloxy-benzenesulfonylamino)-N-hydroxy-propionamide;
2-(4-But-2-ynyloxy-benzenesulfonylamino)-N-hydroxy-3-(4-methoxy-benzylsulfanyl)-propionamide;
2-(4-But-2-ynyloxy-benzenesulfonylamino)-N-1-hydroxy-succinamide;
2-(4-But-2-ynyloxy-benzenesulfonylamino)-3-cyclohexyl-N-hydroxy-propionamide;
2-(4-But-2-ynyloxy-benzenesulfonylamino)-2-cyclohexyl-N-hydroxy-acetamide;
2-(4-But-2-ynyloxy-benzenesulfonylamino)-4-methyl-pentanoic acid hydroxyamide;
2-(4-But-2-ynyloxy-benzenesulfonylamino)-N-hydroxy-4-methylsulfanyl-butyramide;
2-(4-But-2-ynyloxy-benzenesulfonylamino)-N-hydroxy-3-phenyl-propionamide;
1-(4-But-2-ynyloxy-benzenesulfonyl)-pyrrolidine-2-carboxylic acid hydroxyamide;
2-(4-But-2-ynyloxy-benzenesulfonylamino)-N-hydroxy-3-(1H-indol-3-yl)-propionamide;
2-(4-But-2-ynyloxy-benzenesulfonylamino)-N-hydroxy-3-(4-hydroxy-phenyl)-propionamide;
2-(4-But-2-ynyloxy-benzenesulfonylamino)-N-hydroxy-3-methyl-butyramide;
2-(4-But-2-ynyloxy-benzenesulfonylamino)-4-methyl-pentanoic acid hydroxyamide;
2-(4-But-2-ynyloxy-benzenesulfonylamino)-6-(2-chloro-benzylamino)-hexanoic acid hydroxyamide;
2-(4-But-2-ynyloxy-benzenesulfonylamino)-hexanoic acid hydroxyamide;
2-(4-But-2-ynyloxy-benzenesulfonylamino)-N-hydroxy-2-phenyl-acetamide;
3-Benzyloxy-2-(4-but-2-ynyloxy-benzenesulfonylamino)-N-hydroxy-propionamide;
2-(4-But-2-ynyloxy-benzenesulfonylamino)-N-hydroxy-acetamide;
(2R,3S)-2-({[4-(2-Butynyloxy)phenyl]sulfonyl}amino)-N-hydroxy-3-methyl pentanamide;
(2R)-2-({[4-(2-Butynyloxy)phenyl]sulfonyl}amino)-N-hydroxy-3,3-dimethyl-butanamide;
(2S)-2-[(4-But-2-ynyloxy-benzenesulfonyl)-methyl-amino]-N-hydroxy-propionamide;
2-[(4-But-2-ynyloxy-benzenesulfonyl)-ethyl-amino]-N-hydroxy-3-methyl-butyramide;
2-[{[4-(2-Butynyloxy)phenyl]sulfonyl}(2-propynyl)amino]-N-hydroxy-3-methylbutanamide;
2-[(4-But-2-ynyloxy-benzenesulfonyl)-propyl-amino]-N-hydroxy-3-methyl-butyramide;
2-[(4-But-2-ynyloxy-benzenesulfonyl)-(3-phenyl-propyl)-amino]-N-hydroxy-3-methyl-butyramide;
2-[(4-But-2-ynyloxy-benzenesulfonyl)-cyclopropylmethyl-amino]-N-hydroxy-3-methyl-butyramide;
2-[(4-But-2-ynyloxy-benzenesulfonyl)-isobutyl-amino]-N-hydroxy-3-methyl-butyramide;
2-[(4-But-2-ynyloxy-benzenesulfonyl)-pyridin-3-ylmethyl-amino]-N-hydroxy-3-methyl-butyramide;
2-[(4-But-2-ynyloxy-benzenesulfonyl)-methyl-amino]-2-cyclohexyl-N-hydroxy-acetamide;
2-[(4-But-2-ynyloxy-benzenesulfonyl)-pyridin-3-ylmethyl-amino]-2-cyclohexyl-N-hydroxy acetamide;
2-{(4-But-2-ynyloxy-benzenesulfonyl)-[4-(2-piperidin-1-yl-ethoxy)-benzyl]-amino}-2-cyclohexyl-N-hydroxy-acetamide;
2-{{[4-(2-Butynyloxy)phenyl]sulfonyl}[3-(diethylamino)propyl]amino}-N-hydroxy-3-methylbutanamide;
2-{{[4-(2-Butynyloxy)phenyl]sulfonyl}[3-(4-morpholinyl)propyl]amino}-N-hydroxy-3-methylbutanamide;
2-{{[4-(2-Butynyloxy)phenyl]sulfonyl}[3-(4-methyl-1-piperazinyl)propyl]-amino}N-hydroxy-3-methylbutanamide hydrochloride;
2-{{[4-(2-Butynyloxy)phenyl]sulfonyl}[4-(diethylamino)butyl]amino}-N-hydroxy-3-methylbutanamide;
2-{{[4-(2-Butynyloxy)phenyl]sulfonyl}[4-(4-methyl-1-piperazinyl)butyl]amino}-N-hydroxy-3-methylbutanamide;
2-[[[4-(2-Butynyloxy)phenyl]sulfonyl][2-(4-morpholinyl)ethyl]amino]-N-hydroxy-3-methylbutanamide;
2-[{[4-(But-2-ynyloxy)phenyl]sulfonyl}(2-morpholin-4-yl-ethyl)amino]-N-hydroxyacetamide hydrochloride;
2-{{[4-(2-Butynyloxy)phenyl]sulfonyl}[4-(4-methyl-1-piperazinyl)-2-butynyl]amino}-N-hydroxy-3-methylbutanamide;
2-{{[4-(2-Butynyloxy)phenyl]sulfonyl}[4-(diethylamino)-2-butynyl]amino}-N-hydroxy-3-methylbutanamide;
2-{{[4-(2-Butynyloxy)phenyl]sulfonyl}[4-(methylamino)-2-butynyl]amino}-N-hydroxy-3-methylbutanamide;
((2R)-{[4-(2-Butynyloxy)phenyl]sulfonyl}(methyl)amino)[(4-diethylamino)-cyclohexyl]-N-hydroxyethamide;
(2R)-{[4-(2-Butynyloxy)phenyl]sulfonyl}amino-N-hydroxy-2-(4-hydroxycyclo-hexyl)ethanamide;

(2R)-{[4-(2-Butynyloxy)phenyl]sulfonyl}(methyl)amino)-N-hydroxy-2-(4-hydroxycyclohexyl)-ethanamide;
2-[(6-But-2-ynyloxy-pyridine-3-sulfonyl)-methyl-amino]-N-hydroxy-acetamide;
2-[[(4-{[3-(4-Chlorophenyl)-2-propynyl]oxy}phenyl)sulfonyl](methyl)amino]-N-hydroxyacetamide;
N-Hydroxy-2-(methyl{[4-(prop-2-ynylamino)phenyl]suffonyl}amino)acetamide;
2-[(4-But-2-ynylthiophenylsulfonyl)methylamino]-N-hydroxyacetamide;
2-{{[4-(2-Butynyloxy)phenyl]sulfonyl}[4-(4-methyl-1-piperazinyl)-2-yl][4-(4-methyl-1-piperazinyl)-2-butynyl]amino}-N-hydroxypropanamide;
1-[{[4-(2-Butynyloxy)phenyl]sulfonyl}(methyl)amino]-N-sulfonyl](methyl)-amino]-N-hydroxycyclohexanecarboxamide;
1-[{[4-(2-Butynyloxy)phenyl]sulfonyl}(3-pyridinylmethyl)amino]N-hydroxy-cyclohexanecarboxamide;
1-({[4-(2-Butynyloxy)phenyl]sulfonyl}amino)-N-hydroxy-cyclohexane-carboxamide;
1-{{[4-(2-Butynyloxy)phenyl]sulfonyl}amino)-N-ydroxy-cyclopentane-carboxamide;
2-({[4-(2-Butynyloxy)phenyl]sulfonyl)(methyl)amino]-N-hydroxy-3-methyl-3-((2-(4-morpholinylethyl)sulfanyl]-butanamide hydrochloride;
2-({[4-(2-Butynyloxy)phenyl]sulfonyl)(methyl)amino]-N-hydroxy-3-methyl-3-{[2-(4-methyl-1-ethyl-1-piperazinyl)ethyl]sulfanyl}butanamide;
2-({[4-(2-Butynyloxy)phenyl]sulfonyl)(methyl)amino]-N-hydroxy-3-methyl-3-{[2-(diethylamino)ethyl]sulfanyl}butanamide;
2-({[4-(2-Butynyloxy)phenyl]sulfonyl)(methyl)amino]-N-hydroxy-3-methyl-3-{[2-(1-pyrrolidinyl)ethyl]sulfanyl}butanamide;
2-({[4-(2-Butynyloxy)phenyl]sulfonyl)(methyl)amino]-N-hydroxy-3-{[2-(1H-imidazol-1-yl)ethyl]sulfanyl}butanamide;
Methyl 1-[2-({2-[{[4-(2-butynyloxy)phenyl]sulfonyl}(methyl)]amino]-3-(hydroxyamino)-1,1-dimethyl-3-oxopropyl}sulfanyl)ethyl]-2-pyrrolidine-carboxylate;
2-({[4-(2-Butynyloxy)phenyl]sulfonyl)(methyl)amino]-N-hydroxy-3-methyl-3-[(2(4-morpholinylpropyl)sulfanyl]-butanamide;
2-({[4-(2-Butynyloxy)phenyl]sulfonyl)(methyl)amino]-N-hydroxy-3-methyl-3-{[2(4-methyl-1-ethyl-1-pipetazinyl)propyl]sulfanyl}butanamide;
2-({[4-(2-Butynyloxy)phenyl]sulfonyl)(methyl)amino]-N-hydroxy-3-methyl-3-{[2-(diethylamino)propyl]sulfanyl}butanamide;
2-[(4-But-2-ynyloxy-benenesulfonyl)-methyl-amino]-N-hydroxy-3-methyl-3-methylsulfanyl-butyramide;
2-[(4-But-2-ynyloxy-benenesulfonyl)-methyl-amino]-N-hydroxy-3-methyl-3-ethylsulfanyl-butyramide;
2-[(4-But-2-ynyloxy-benenesulfonyl)-methyl-amino]-N-hydroxy-3-methyl-3-propylsulfanyl-butyramide;
2-[(4-But-2-ynyloxy-benenesulfonyl)-methyl-amino]-N-hydroxy-3-methyl-3-(pyridin-3-ylmethylsulfanyl)-butyramide;
2-[(4-But-2-ynyloxy-benenesulfonyl)-methyl-amino]-N-hydroxy-3-methyl-3-benzylsulfanyl-butyramide;
2-[(4-But-2-ynyloxy-benenesulfonyl)-methyl-amino]-N-hydroxy-3-(methylsulfanyl)-butyramide;
2-[(4-But-2-ynyloxy-benenesulfonyl)-methyl-amino]-N-hydroxy-3-(pyridin-3-ylmethylsulfanyl)-butyramide;
3-(Benzylthio)-2-[[[4-(2-butynyloxy)phenyl]sulfonyl]methylamino]-N-hydroxy-propanamide;
3-(Benzylthio)-2-[[[4-(2-butynyloxy)phenyl]sulfonyl]pyridin-3-ylmethylamino]-N-hydroxypropanamide;
2-[[[4-(2-Butynyloxy-phenyl]sulfonyl]amino]-N-hydroxy-3-methyl-(3-methylthio)-butyramide;
2-[(4-But-2-ynyloxy-benenesulfonyl)-amino]-N-hydroxy-3-methyl-3-ethylsulfanyl-butyramide;
2-[(4-But-2-ynyloxy-benenesulfonyl)-amino]-N-hydroxy-3-methyl-3-propylsulfanyl-butyramide;
2-[(4-Butynyloxy-phenylsulfonyl)-amino]-N-hydroxy-3-methyl-[(3-pyridinyl-methyl)thio]butyramide;
2-[(4-Butynyloxy-phenyl)sulfonyl)-amino]-N-hydroxy-3-methyl-(3-benzyl-sulfanyl)butyramide;
2-({[4-(2-Butynyloxy)phenyl]sulfonyl}amino-N-hydroxy-3-{[(-methyl-1H-imidazol-2-yl]methylsulfanyl}butanamide;
2-({[4-(2-butynyloxy)phenyl]sulfonyl}amino-N-hydroxy-3-methyl-3-{[2-(4-morpholinyl)ethyl]sulfanyl}butanamide;
tert-Butyl-{[2-({[4-2-butynyloxy)phenyl]sulfonyl}amino)-3-(hydroxyamino)-1,1-dimethyl-3-oxopropyl]sulfanyl}acetate;
tert-Butyl {[2-({[4-2-butynyloxy)phenyl]sulfonyl}amino)-3-(hydroxyamino)-1,1-dimethyl-3-oxopropyl]sulfanyl acetic acid, sodium salt;
2-[(4-Butynyloxy-phenylsulfonyl)-amino]-N-hydroxy-3-(methylthio)-propanamide;
2-[[4-Butynyloxy-phenylsulfonyl]-amino]-N-hydroxy-3-(benzylthio)-propanamide;
2-[[4-Butynyloxy-phenylsulfonyl]-amino]-N-hydroxy-3-(pyridinylthio)-propanamide;
2-({[4-(2-Butynyloxy)phenyl]sulfonyl}amino)-N-hydroxy-3-[(Z)-11-tetradecenyisulfanyl]propanamide;
(2S)-2-({[4-(2-Butynyloxy)phenyl]sulfonyl}amino)-N-hydroxy-3-[(3-hydroxy-propyl)sulfanyl]-3-methylbutanamide;
(2S)-2-({[4-(2-Butynyloxy)phenyl]sulfonyl}amino)-N-hydroxy-3-[(3-hydroxy-propyl)sulfanyl]-3-propanamide;
(3S)-4-({[4-(2-Butynyloxy)phenyl]sulfonyl}-N-hydroxy-2,2-dimethyl-1,4-thiazepane-3-carboxamide;
(3S)-4-({[4-(2-Butynyloxy)phenyl]sulfonyl}-N-hydroxy-1,4-thiazepane-3-carboxamide;
(3S)-4-({[4-(2-Butynyloxy)phenyl]sulfonyl}-N-hydroxy-1,4-thiazepane-3-carboxamide 1,1-dioxide;
2-({[4-(2-Butynyloxy)phenyl]sulfonyl}amino)-N-hydroxy-2-(4-hydroxy-phenyl)acetamide;
2-({[4-(2-Butynyloxy)phenyl]sulfonyl}amino)-N-hydroxy-2-[4-(2-propynyloxy)-phenyl]acetamide;
2-{{[4-(2-Butynyloxy)phenyl]sulfonyl}(methyl)amino]-N-hydroxy-2-(4-methoxyphenyl)acetamide;
2-{{[4-(2-Butynyloxy)phenyl]sulfonyl}(methyl)amino]-N-hydroxy-2-{4-[2-(4-morpholinyl)ethoxy]phenyl}acetamide;
tert-Butyl 2-{4-[1-[{[4-(2-butynyloxy)phenyl]sulfonyl}(methyl)amino]-2-(hydroxyamino)-2-oxoethyl]phenoxy}ethylcarbamate;
2-[4-(2-Aminoethoxy)phenyl]-2-[{[4-(2-butynyloxy)phenyl]sulfonyl}-(methyl)amino]-N-hydroxyacetamide;
2-[{[4-(2-Butynyloxy)phenyl]sulfonyl}(methyl)amino]-2-{4-[2-(dimethylamino)-ethoxy]phenyl}-N-hydroxyacetamide;
2-[{[4-(2-Butynyloxy)phenyl]sulfonyl}(methyl)amino]-N-hydroxy-2-{4-[2-(1-pyrrolidinyl)ethoxy]phenyl}acetamide;
2-[{[4-(2-Butynyloxy)phenyl]sulfonyl}(methyl)amino]-N-hydroxy-2-{4-[2-(2-oxo-1-pyrrolidinyl)ethoxy]phenyl}acetamide;

tert-Butyl 4-(2-{4-[1-[{[4-(2-butynyloxy)phenyl]sulfonyl}(methyl)amino]-2-(hydroxyamino)-2-oxoethyl]phenoxy}ethyl)-1-piperazinecarboxylate;

2-[{[4-(2-Butynyloxy)phenyl]sulfonyl}(methyl)amino]-N-hydroxy-2-{4-[2-(1-piperazinyl)ethoxy]phenyl}acetamide;

tert-Butyl 3-{4-[1-[{[4-(2-butynyloxy)phenyl]sulfonyl}(methyl)amino]-2-(hydroxyamino)-2-oxoethyl]phenoxy}propylcarbamate;

2-[4-(3-Aminopropoxy)phenyl]-2-[{[4-(2-butynyloxy)phenyl]-sulfonyl}(methyl)amino]-N-hydroxyacetamide;

tert-Butyl (3S)-3-{4-[(1R)-1-[{[4-(2-butynyloxy)phenyl]sulfonyl}-(methyl)amino]-2-(hydroxyamino)-2-oxoethyl]phenoxy}-1-pyrrolidine-carboxylate;

(2R)-2-[{[4-(2-Butynyloxy)phenyl]sulfonyl}(methyl)amino]-N-hydroxy-2-{4-[(3S)-pyrrolidinyloxy]phenyl}ethanamide;

tert-Butyl (2-{4-[1-({[4-(2-butynyloxy)phenyl]sulfonyl}(methyl)amino)-2-(hydroxyamino)-2-oxoethyl)phenoxy]ethyl)-(methyl)carbamate;

2-({[4-(2-Butynyloxy)phenyl]sulfonyl}(methyl)amino)-N-hydroxy-2-{4-[2-(methylamino)ethoxy]phenyl}acetamide;

Ethyl 3-{4-[1-[{[4-(2-butynyloxy)phenyl]sulfonyl}(methyl)amino]-2-(hydroxyamino)-2-oxoethyl]phenoxy}propylcarbamate;

2-{4-[3-(Acetylamino)propoxy]phenyl}-2-[{[4-(2-butynyloxy)phenyl]-sulfonyl}(methyl)amino]-N-hydroxyacetamide;

Butyl-3-{4-[1-[{[4-(2-butynyloxy)phenyl]sulfonyl}(methyl)amino]-2-(hydroxyamino)-2-oxoethyl]phenoxy}propylcarbamate;

Benzyl-3-{4-[1-[{[4-(2-butynyloxy)phenyl]sulfonyl}(methyl)amino]-2-(hydroxyamino)-2-oxoethyl]phenoxy}propylcarbamate;

2-[{[4-(2-Butynyloxy)phenyl]sulfonyl}(methyl)amino]-N-hydroxy-2-(4-{3-[(methylsulfonyl)amino]propoxy}phenyl)acetamide;

2-(4-{3-[(Anilinocarbonyl)amino]propoxy}phenyl)-2-[{[4-(2-butynyloxy)-phenyl]sulfonyl}(methyl)amino]-N-hydroxyacetamide;

tert-Butyl 2-{4-[(1R)-1-({[4-(2-butynyloxy)phenyl]sulfonyl}amino)-2-(hydroxyamino)-2-oxoethyl]phenoxy}ethylcarbamate;

(2R)-2-[4-(2-Aminoethoxy)phenyl]-2-({[4-(2-butynyloxy)phenyl]-sulfonyl}amino)-N-hydroxyethanamide;

(2R)-2-{4-[2-(Acetylamino)ethoxy]phenyl}-2-({[4-(2-butynyloxy)phenyl]-sulfonyl}amino)-N-hydroxyethanamide;

tert-Butyl 4-(2-{4-[1-({[4-(2-butynyloxy)phenyl]sulfonyl}amino)-2-(hydroxyamino)-2-oxoethyl)phenoxy]ethyl)-1-piperazinecarboxylate;

tert-Butyl 4-(2-{4-[1-({[4-(2-butynyloxy)phenyl]sulfonyl}amino)-2-(hydroxyamino)-2-oxoethyl)phenoxy]ethyl)-(methyl)carbamate;

2-{[4-(2-Butynyloxy)phenyl]sulfonyl}amino)-N-hydroxy-2-{4-[2-(methylamino)ethoxy]phenyl})acetamide;

2-({[4-(2-Butynyloxy)phenyl]sulfonyl}amino)-N-hydroxy-2-{4-[2-(1-pyrrolidinyl)ethoxy]phenyl}acetamide;

2-({[4-(2-Butynyloxy)phenyl]sulfonyl}amino)-N-hydroxy-2-{4-[2-(4-morpholinyl)ethoxy]phenyl}acetamide;

2-({[4-(2-Butynyloxy)phenyl]sulfonyl}amino){4-[2-(dimethylamino)ethoxy]-phenyl}-N-hydroxyacetamide;

2-({[4-(2-Butynyloxy)phenyl]sulfonyl}amino)-N-hydroxy-2-{4-[2-(4-methyl-1,3-thiazol-5-yl)ethoxy]phenyl}acetamide;

2-({[4-(2-Butynyloxy)phenyl]sulfonyl}amino)-N-hydroxy-2-(4-{2-[2-(2-thoxyethoxy)ethoxy]ethoxy}phenyl)acetamide;

2-({[4-(2-Butynyloxy)phenyl]sulfonyl}amino)-N-hydroxy-2-{4-[2-(2-methoxy-ethoxy)ethoxy]phenyl}acetamide;

2-[{[4-(2-Butynyloxy)phenyl]sulfonyl}(methyl)amino]-N-hydroxy-2-phenyl-acetamide;

2-[{[4-(2-Butynyloxy)phenyl]sulfonyl}(methyl)amino]-2-(4-chlorophenyl)-N-hydroxyacetamide;

2-[{[4-(2-Butynyloxy)phenyl]sulfonyl}(methyl)amino]-5-[(4-chlorophenyl)-sulfanyl]-N-hydroxypentanamide;

1-(4-But-2-ynyloxy-benzenesulfonyl)-piperazine-2-carboxylic acid hydroxyamide;

1-(4-But-2-ynyloxy-benzenesulfonyl)-4-(morpholine-4-carbonyl)-piperazine-2-carboxylic acid hydroxyamide;

4-(4-But-2-ynyloxy-benzenesulfonyl)-piperazine-1,3-dicarboxylic acid 1-diethylamide 3-hydroxyamide;

1-(4-But-2-ynyloxy-benzenesulfonyl)-4-(pyrrolidine-1-carbonyl)-piperazine-2-carboxylic acid hydroxyamide;

4-(4-But-2-ynyloxy-benzenesulfonyl)-piperazine-1,3-dicarboxylic acid 1-diisopropylamide 3-hydroxyamide;

Benzyl 4-{[4-(2-butynyloxy)phenyl]sulfonyl}-3-[(hydroxyamino)carbonyl]-1-piperazinecarboxylate;

4-(4-But-2-ynyloxy-benzenesulfonyl)-piperazine-1,3-dicarboxylic acid 3-hydroxyamide 1-(methyl-phenyl-amide);

4-{[4-(2-Butynyloxy)phenyl]sulfonyl}-N-3-hydroxy-N-1-(4-methoxyphenyl)-1,3-piperazinedicarboxamide;

4-{[4-(2-Butynyloxy)phenyl]sulfonyl}-N-1-(4-fluorophenyl)-N-3-hydroxy-1,3-piperazinedicarboxamide;

4-{[4-(2-Butynyloxy)phenyl]sulfonyl}-N-1-(3,5-dichlorophenyl)-N-3-hydroxy-1,3-piperazinedicarboxamide;

4-Acetyl-1-(4-but-2-ynyloxy-benzenesulfonyl)-piperazine-2-carboxylic acid hydroxyamide;

1-(4-But-2-ynyloxy-benzenesulfonyl)-4-propionyl-piperazine-2-carboxylic acid hydroxyamide;

1-(4-But-2-ynyloxy-benzenesulfonyl)-4-(thiophene-2-carbonyl)-piperazine-2-carboxylic acid hydroxyamide;

1-(4-But-2-ynyloxy-benzenesulfonyl)-4-methanesulfonyl-piperazine-2-carboxylic acid hydroxyamide;

4-(4-But-2-ynyloxy-benzenesulfonyl)-3-hydroxycarbamoyl-piperazine-1-carboxylic acid methyl ester;

{2-[4-(4-But-2-ynyloxy-benzenesulfonyl)-3-hydroxycarbamoyl-piperazin-1-yl]-2-oxo-ethyl{-carbamic acid tert-butyl ester;

4-Aminoacetyl-1-(4-but-2-ynyloxy-benzenesulfonyl)-piperazine-2-carboxylic acid hydroxyamide;

1-{[4-(2-Butynyloxy)phenyl]sulfonyl}-N-hydroxy-4-[(2,2,5-trimethyl-1,3-dioxan-5-yl)carbonyl]-2-piperazinecarboxamide;

1-{[4-(2-Butynyloxy)phenyl]sulfonyl}-N-hydroxy-4-[3-hydroxy-2-(hydroxy-methyl)-2-methylpropanoyl-2-piperazinecarboxamide;

4-(4-Bromo-benzyl)-1-(4-but-2-ynyloxy-benzenesulfonyl)-piperazine-2-carboxylic acid hydroxyamide;

1-(4-But-2-ynyloxy-benzenesulfonyl)-4-pyridin-3-ylmethyl-piperazine-2-carboxylic acid hydroxyamide;

(3S)-4-({[4-(2-Butynyloxy)phenyl]sutfonyl)-2,2-dimethyl-thiomorpholine-3-carboxylic acid hydroxyamide;

9-({[4-(2-Butynyloxy)phenyl]sulfonyl}-N-hydroxy-6-thia-9-azaspiro[4,5]-decane-10-carboxamide;

9-({[4-(2-Butynyloxy)phenyl]sulfonyl}-N-hydroxy-1-thia-4-azaspiro[5,5]-undecane-5-carboxamide;

4-({[4-(2-Butynyloxy)phenyl]sulfonyl)-2,2-diethyl-thiomorpholine-3-carboxylic acid hydroxyamide;

4-({[4-(2-Butynyloxy)phenyl]sulfonyl)-N-hydroxy-thiomorpholine-3-carboxamide;

4-([4-(2-Butynyloxy)phenyl]sulfonyl}-N-hydroxy-3-morpholinecarboxamide;
9-Benzyl-4-{[4-(2-butynyloxy)phenyl]sulfonyl}-N-hydroxy-1-thia-4,9-diazaspiro[5.5]undecane-5-carboxamide;
9-Methyl-4-{[4-(2-butynyloxy)phenyl]sulfonyl{-N-hydroxy-1-thia-4,9-diazaspiro[5.5]undecane-5-carboxamide;
N-Hydroxy-2,2-dimethyl-4-[(4-{[5-(tetrahydro-2H-pyran-2-yloxy)-2-pentynyl]oxy}phenyl)sulfonyl]-3-thiomorpholine carboxamide;
N-Hydroxy-4-({4-[(5-hydroxy-2-pentynyl)oxy]phenyl}sulfonyl)-2,2-dimethyl-3-thiomorpholine carboxamide;
tert-Butyl 5-[4-({3-[(hydroxyamino)carbonyl]-2,2-dimethyl-4-thiomorpholinyl}sulfonyl)phenoxy]-3-pentynylcarbamate;
4-({4-[(5-Amino-2-pentynyl)oxy]phenyl}sulfonyl)-N-hydroxy-2,2-dimethyl-3-thiomorpholine carboxamide;
4-[(4-{[4-(Benzyloxy)-2-butynyl]oxy}phenyl)sulfonyl]-N-hydroxy-2,2-dimethyl-3-thiomorpholine carboxamide;
N-Hydroxy-2,2-dimethyl-4-[(4-{[6-(tetrahydro-2H-pyran-2-yloxy)-2-hexynyl]-oxy}phenyl)sulfonyl]-3-thiomorpholine carboxamide;
N-Hydroxy-4-({4-[(6-hydroxy-2-hexynyl)oxy]phenyl}sulfonyl)-2,2-dimethyl-3-thiomorpholine carboxamide;
tert-Butyl 6-[4-({(3S)-3-[(hydroxyamino)carbonyl]-2,2-dimethyl-thiomorpholinyl}sulfonyl)phenoxy]-4-hexynylcarbamate;
(3S)-4-({4-[(6-Amino-2-hexynyl)oxy]phenyl}sulfonyl)-N-hydroxy-2,2-dimethyl-3-thiomorpholine carboxamide;
tert-Butyl 7-[4-({(3S)-3-[(hydroxyamino)carbonyl]-2,2-dimethyl-thiomorpholinyl}sulfonyl)phenoxy]-5-heptynylcarbamate;
(3S)-4-({4-[(7-Amino-2-heptynyl)oxy]phenyl}sulfonyl)-N-hydroxy-2,2-dimethyl-3-thiomorpholine carboxamide;
(3S)-N-Hydroxy-2,2-dimethyl-4-({4-[(3-phenyl-2-propynyl)oxy]-phenyl}sulfonyl)-3-thiomorpholine carboxamide;
(3S)-4-{[4-(2-Butynyloxy)phenyl]sulfonyl}-N-hydroxy-2,2-dimethyl-3-thiomorpholine carboxamide (1S)-oxide;
(3S)-4-{[4-(2-Butynyloxy)phenyl]sulfonyl}-N-hydroxy-2,2-dimethyl-3-thiomorpholine carboxamide (1R)-oxide;
(3S)-4-{[4-(2-Butynyloxy)phenyl]sulfonyl}-N-hydroxy-2,2-dimethyl-3-thiomorpholine Carboxamide-1,1-dioxide;
(3S)-N-Hydroxy-2,2-dimethyl-4-{[4-(2-propynyloxy)phenyl]sulfonyl}-3-thiomorpholine carboxamide;
(3S)-N-Hydroxy-2,2-dimethyl-4-{[4-(2-pentynyloxy)phenyl]sulfonyl}-3-thiomorpholine carboxamide;
(3S)-N-Hydroxy-4-({4-[(4-hydroxy-2-butynyl)oxy]phenyl}sulfonyl)-2,2-dimethyl-3-thiomorpholine carboxamide;
4-[4-({(3S)-3-[(Hydroxyamino)carbonyl]-2,2-dimethylthiomorpholinyl}-sulfonyl)phenoxy]-2-butynyl acetate;
(3S)-N-Hydroxy-4-({4-[(6-hydroxy-2,4-hexadiynyl)oxy]phenyl}sulfonyl)-2,2-dimethyl-3-thiomorpholine carboxamide;
(3S)-N-Hydroxy-2,2-dimethyl-4-{[4-(2,4-pentadiynyloxy)phenyl]sulfonyl}-3-thiomorpholine carboxamide;
(3S)-4-({4-[(4-Fluoro-2-butynyl)oxy]phenyl}sulfonyl)-N-hydroxy-2,2-dimethyl-3-thiomorpholine carboxamide;
4-({4-[(4-Amino-2-butynyl)oxy]phenyl}sulfonyl)-N-hydroxy-2,2-dimethyl-3-biomorpholine carboxamide;
tert-Butyl-4-[4-({3-[(hydroxyamino)carbonyl]-2,2-dimethyl-4-thiomorpholinyl}-sulfonyl)phenoxy]-2-butynylcarbamate;
tert-Butyl 4-[4-({3-[(hydroxyamino)carbonyl]-2,2-dimethyl-4-thiomorpholinyl}-sulfonyl)phenoxy]-2-butynyl(methyl)carbamate;
7-[4-({(3S)-3-[(Hydroxyamino)carbonyl]-2,2-dimethylthiomorpholinyl}-sulfonyl)phenoxy]-5-heptynyl acetate;
(3S)-N-Hydroxy-4-({4-[(7-hydroxy-2-heptynyl)oxy]phenyl}sulfonyl)-2,2-dimethyl-3-thiomorpholinecarboxamide;
(3S,5S)-4-{[4-(2-Butynyloxy)phenyl]sulfonyl}-N-hydroxy-2,2,5-trimethyl-3-thiomorpholinecarboxamide;
(3S,5R)-4-{[4-(2-Butynyloxy)phenyl]sulfonyl}-N-hydroxy-2,2,5-trimethyl-3-thiomorpholinecarboxamide;
(3S,6S)-4-{[4-(2-Butynyloxy)phenyl]sulfonyl}-N-hydroxy-2,2,6-trimethyl-3-thiomorpholinecarboxamide;
tert-Butyl{(2R,5S)-4-{[4-(2-butynyloxy)phenyl]sulfonyl}-5-[(hydroxyamino)-carbonyl]-6,6-dimethylthiomorpholinyl}methylcarbamate;
tert-Butyl{(2S,5S)-4-{[4-(2-butynyloxy)phenyl]sulfonyl}-5-[(hydroxyamino)-carbonyl]-6,6-dimethylthiomorpholinyl}methylcarbamate;
(3S,6R)-Trans-6-(aminomethyl)-4-{[4-(2-butynyloxy)phenyl]sulfonyl}-N-hydroxy-2,2-dimethyl-3-thiomorpholinecarboxamide hydrochloride;
(3S3,6S)-Cis-6-(aminomethyl)-4-{[4-(2-butynyloxy)phenyl]sulfonyl}-N-hydroxy-2,2-dimethyl-3-thiomorpholinecarboxamide hydrochloride;
tert-Butyl{(2S,5S)-4-{[4-(2-butynyloxy)phenyl]sulfonyl}-5-[(hydroxyamino)-carbonyl]-6,6-dimethylthiomorpholinyl}acetate;
{(2S,5S)-4-{[4-(2-Butynyloxy)phenyl]sulfonyl}-5-[(hydroxyamino)carbonyl]-6,6-dimethylthiomorpholinyl}acetic acid;
(3S,6S)-4-{[4-(2-Butynyloxy)phenyl]sulfonyl}-N-hydroxy-6-[2-(hydroxyamino)-2-oxoethyl]-2,2-dimethyl-3-thiomorpholinecarboxamide;
(3S,6S)-6-(2-Amino-2-oxoethyl)-4-{[4-(2-butynyloxy)phenyl]sulfonyl}-N-hydroxy-2,2-dimethyl-3-thiomorpholinecarboxamide;
(3S3,6S)-4-{[4-(2-Butynyloxy)phenyl]sulfonyl}-6-[2-(dimethylamino)-2-oxoethyl]-N-hydroxy-2,2-dimethyl-3-thiomorpholinecarboxamide;
(3S,6S)-4-{[4-(2-Butynyloxy)phenyl]sulfonyl}-N-hydroxy-2,2-dimethyl-6-[2-(4-morpholinyl)-2-oxoethyl]-3-thiomorpholinecarboxamide;
(3S,6S)-4-{[4-(2-Butynyloxy)phenyl]sulfonyl}-N-hydroxy-2,2-dimethyl-6-[2-(4-methyl-1-piperazinyl)-2-oxoethyl]-3-thiomorpholinecarboxamide hydrochloride;
(3S,6S)-4-{[4-(2-Butynyloxy)phenyl]sulfonyl}-6-(2-{[2-(dimethylamino)-ethyl]amino}-2-oxoethyl)-N-hydroxy-2,2-dimethyl-3-thiomorpholine-carboxamide;
Methyl (3S,6S)-6-{[(tert-butoxycarbonyl)amino]methyl}-4-{[4-(2-butynyloxy)phenyl]sulfonyl}-2,2-dimethyl-3-thiomorpholinecarboxylate;
(4S)-3-{[4-(2-Butynyloxy)phenyl]sulfonyl}-N-hydroxy-5,5-dimethyl-1,3-thiazolidine-4-carboxamide;
tert-Butyl 4-({[4-(2-butynyloxy)phenyl]sulfonyl}amino)-4-[(hydroxyamino)-carbonyl]-1-piperidinecarboxylate;
4-({[4-(2-Butynyloxy)phenyl]sulfonyl}amino)-N-hydroxy-4-piperidine-carboxamide;
1-Benzoyl-4-{[4-(2-butynyloxy)phenyl]sulfonyl}-N-hydroxy-1,4-diazepane-5-carboxamide;
1-Benzyl-4-{[4-(2-butynyloxy)phenyl]sulfonyl}-N-hydroxy-1,4-diazepane-5-carboxamide;
tert-Butyl 4-{[4-(2-butynyloxy)phenyl]sulfonyl}-5-[(hydroxyamino)carbonyl]-1,4-diazepane-1-carboxylate;
4-{[4-(2-Butynyloxy)phenyl]sulfonyl}-N-hydroxy-1,4-diazepane-5-carboxamide;

4-{[4-(2-Butynyloxy)phenyl]sulfonyl}-N-hydroxy-1-methyl-1,4-diazepane-5-carboxamide;
4-{[4-(2-Butynyloxy)phenyl]sulfonyl}-N-hydroxy-1,4-thiazepine-5-carboxamide;
(2R)-5-(Acetylamino)-2-({[4-(but-2-ynyloxy)phenyl]sulfonyl}amino)-N-hydroxypentanamide;
N-[(4R)-4-({[4-(But-2-ynyloxy)phenyl]sulfonyl}amino)-5-(hydroxyamino)-5-oxopentyl]thiophene-2-carboxamide;
(2R)-2-({[4-(But-2-ynyloxy)phenyl]sulfonyl}amino)-5-{[(ethylamino)carbonyl]-amino}-N-hydroxypentanamide;
(2R)-5-[(Aminocarbonyl)amino]-2-({[4-(but-2-ynyloxy)phenyl]sulfonyl}-amino)-N-hydroxypentanamide;
Octyl (4R)-4-({[4-(but-2-ynyloxy)phenyl]sulfonyl}amino)-5-(hydroxyamino)-5-oxopentylcarbamate;
4-Methoxyphenyl (4R)-4-({[4-(but-2-ynyloxy)phenyl]sulfonyl}amino)-5-(hydroxyamino)-5-oxopentylcarbamate;
(2R)-2-({[4-(But-2-ynytoxy)phenyl]sulfonyl}amino)-5-{[(diethylamino)-carbonyl]amino}-N-hydroxypentanamide;
(2R)-2-({[4-(But-2-ynyloxy)phenyl]sulfonyl}amino)-N-hydroxy-5-{[(methylanilino)carbonyl]amino}pentanamide;
(2R)-2-({[4-(But-2-ynyloxy)phenyl]sulfonyl}amino)-N-hydroxy-5-{[(1-methyl-1H-imidazol-4-yl)sulfonyl]amino}pentanamide;
(2R)-2-({[4-(But-2-ynyloxy)phenyl]sulfonyl}amino)-N-hydroxy-5-[(2-morpholin-4-ylacetyl)amino]pentanamide;
(2R)-2-({[4-(But-2-ynyloxy)phenyl]sulfonyl}amino)-N-hydroxy-5-{[2-(4-methylpiperazin-1-yl)acetyl]amino}pentanamide;
(2R)-5-{[2-(Benzylamino)acetyl]amino}-2-({[4-(but-2-ynyloxy)phenyl]-sulfonyl}amino)-N-hydroxypentanamide;
(3S)-4-{[4-(2-Butynyloxy)phenyl]sulfonyl}-N-hydroxy-2,2-dimethyl-3,4-dihydro-2H-1,4-thiazine-3-carboxamide;
(2R)-2-({[4-(2-Butynyloxy)phenyl]sulfonyl}amino)-N-hydroxy-5-[(imino{[(4-{[(4-methoxy-2,3,6-trimethylphenyl)sulfonyl]amino}methyl)amino]pentanamide;
(2R)-2-(4-But-2-ynyloxy-benzenesulfonylamino)-5-guanidino-pentanoic acid hydroxyamide;
(2R)-2-({[4-(2-Butynyloxy)phenyl]sulfonyl}amino)-N-hydroxy-5-[(imino{[(4-methylphenyl)sulfonyl]amino}methyl)amino]pentanamide;
(3R)-3-({[4-(But-2-ynyloxy)phenyl]sulfonyl}amino)-4-(hydroxyamino)-4-oxobutanoic acid;
(2S)-3-(tert-Butylthio)-2-({[4-(but-2-ynyloxy)phenyl]sulfonyl}amino)-N-hydroxypropanamide;
(2S)-3-{[(Acetylamino)methyl]thio}2-({[4-(but-2-ynyloxy)phenyl]sulfonyl}amino)-N-hydroxypropanamide;
(2S)-2-({[4-(But-2-ynyloxy)phenyl]sulfonyl}amino)-N-hydroxy-3-[(4-methylbenzyl)thio]propanamide;
(2S)-2-({[4-(But-2-ynyloxy)phenyl]sulfonyl}amino)-N-hydroxy-3-[(4-methoxybenzyl)thio]propanamide;
(2R)-2-({[4-(But-2-ynyloxy)phenyl]sulfonyl}amino)-N-hydroxypentanediamide;
(4R)-4-({[4-(But-2-ynyloxy)phenyl]sulfonyl}amino)-5-(hydroxyamino)-5-oxopentanoic acid;
(2R)-2-({[4-(But-2-ynyloxy)phenyl]sulfonyl}amino)-N-hydroxy-4-phenyl-butanamide;
(2R)-2-({[4-(But-2-ynyloxy)phenyl]sulfonyl}amino)-N-hydroxy-3-(1H-imidazol-5-yl)propanamide;
(2R,4S)-1-{[4-(But-2-ynyloxy)phenyl]sulfonyl}-N,4-dihydroxypyrrolidine-2-carboxamide;
(2R)-6-Amino-2-({[4-(but-2-ynyloxy)phenyl]sulfonyl}amino)-N-hydroxy-hexanamide;
Benzyl (5R)-5-({[4-(but-2-ynyloxy)phenyl]sulfonyl}amino)-6-(hydroxyamino)-6-oxohexylcarbamate;
(2R)-2-({[4-(But-2-ynyloxy)phenyl]sulfonyl}amino)-N-hydroxy-3-(1-naphthyl)-propanamide;
(2R)-2-({[4-(But-2-ynyloxy)phenyl]sulfonyl}amino)-N-hydroxy-3-(2-naphthyl)-propanamide;
(2R)-2-({[4-(But-2-ynyloxy)phenyl]sulfonyl}amino)-N-hydroxyhexanamide;
(2R)-2-({[4-(But-2-ynyloxy)phenyl]sulfonyl}amino)-N-hydroxypentanamide;
(2R)-5-Amino-2-({[4-(but-2-ynyloxy)phenyl]sulfonyl}amino)-N-hydroxypentanamide;
(2R)-2-({[4-(But-2-ynyloxy)phenyl]sulfonyl}amino)-3-(3,4-difluorophenyl)-N-hydroxypropanamide;
(2R)-2-({[4-(But-2-ynyloxy)phenyl]sulfonyl}amino)-3-(4-fluorophenyl)-N-hydroxypropanamide;
(2R)-2-({[4-(But-2-ynyloxy)phenyl]sulfonyl}amino)-N-hydroxy-3-(4-nitrophenyl)-propanamide;
(2R)-1-{[4-(But-2-ynyloxy)phenyl]sulfonyl}-N-hydroxypiperidine-2-carboxamide;
(2R)-2-({[4-(But-2-ynyloxy)phenyl]sulfonyl}amino)-N,3-dihydroxypropanamide;
(2R)-3-(Benzyloxy)-2-({[4-(but-2-ynyloxy)phenyl]sulfonyl}amino)-N-hydroxy-propanamide;
(2R)-2-({[4-(But-2-ynyloxy)phenyl]sulfonyl}amino)-N-hydroxy-3-thien-2-yl-propanamide;
(2R,3S)-2-({[4-(But-2-ynyloxy)phenyl]sulfonyl}amino)-N,3-dihydroxybutanamide;
(2R,3S)-3-(Benzyloxy)-2-({[4-(but-2-ynyloxy)phenyl]sulfonyl}amino)-N-hydroxybutanamide;
(4S)-3-{[4-(But-2-ynyloxy)phenyl]sulfonyl}-N-hydroxy-1,3-thiazolidine-4-carboxamide;
(3R)-2-{[4-(But-2-ynyloxy)phenyl]sulfonyl}-N-hydroxy-1,2,3,4-tetrahydro-isoquinoline-3-carboxamide;
(2R)-3-[4-(Benzyloxy)phenyl]-2-({[4-(but-2-ynyloxy)phenyl]sulfonyl}amino)-N-hydroxypropanamide;
(2R)-2-({[4-(But-2-ynyloxy)phenyl]sulfonyl}amino)-N-hydroxy-2-phenyl-ethanamide;
(2R)-5-(Acetylamino)-2-({[4-(but-2-ynyloxy)phenyl]sulfonyl}amino)-N-hydroxy-pentanamide;
N-[(4R)-4-({[4-(But-2-ynyloxy)phenyl]sulfonyl}amino)-5-(hydroxyamino)-5-oxopentyl]-1H-benzimidazole-5-carboxamide;
N-[(4R)-4-({[4-(But-2-ynyloxy)phenyl]sulfonyl}amino)-5-(hydroxyamino)-5-oxopentyl]benzamide;
4-Bromo-N-[(4R)-4-({[4-(but-2-ynyloxy)phenyl]sulfonyl}amino)-5-(hydroxy-amino)-5-oxopentyl]benzamide;
(2R)-2-({[4-(But-2-ynyloxy)phenyl]sulfonyl}amino)-5-(butyrylamino)-N-hydroxypentanamide;
N-[(4R)-4-({[4-(But-2-ynyloxy)phenyl]sulfonyl}amino)-5-(hydroxyamino)-5-oxopentyl]-3-chlorothiophene-2-carboxamide;
N-[(4R)-4-({[4-(But-2-ynyloxy)phenyl]sulfonyl}amino)-5-(hydroxyamino)-5-oxopentyl]-4-chlorobenzamide;
N-[(4R)-4-({[4-(But-2-ynyloxy)phenyl]sulfonyl}amino)-5-(hydroxyamino)-5-oxopentyl]cyclohexanecarboxamide;
(2R)-2-({[4-(But-2-ynyloxy)phenyl]sulfonyl}amino)-5-{[2-(3,4-dichlorophenyl)-acetyl]amino}-N-hydroxypentanamide;
N-[(4R)-4-({[4-(But-2-ynyloxy)phenyl]sulfonyl}amino)-5-(hydroxyamino)-5-oxopentyl]-2,5-dimethyl-3-furamide;
N-[(4R)-4-({[4-(But-2-ynyloxy)phenyl]sulfonyl}amino)-5-(hydroxyamino)-5-oxopentyl]-3,5-dimethylisoxazoie-4-carboxamide;

(2R)-2-({[4-(But-2-ynyloxy)phenyl]sulfonyl}amino)-N-hydroxy-5-[(3-phenyl-propanoyl)amino]pentanamide;
N-[(4R)-4-({[4-(But-2-ynyloxy)phenyl]sulfonyl}amino)-5-(hydroxyamino)-5-oxopentyl]isonicotinamide;
N-[(4R)-4-({[4-(But-2-ynyloxy)phenyl]sulfonyl}amino)-5-(hydroxyamino)-5-oxopentyl]nicotinamide;
N-[(4R)-4-({[4-(But-2-ynyloxy)phenyl]sulfonyl}amino)-5-(hydroxyamino)-5-oxopentyl]-2-methoxybenzamide;
N-[(4R)-4-({[4-(But-2-ynyloxy)phenyl]sulfonyl}amino)-5-(hydroxyamino)-5-oxopentyl]-4-methoxybenzamide;
(2R)-2-({[4-(But-2-ynyloxy)phenyl]sulfonyl}amino)-N-hydroxy-5-{[2-(4-nitrophenyl)acetyl]amino}pentanamide;
(2R)-2-({[4-(But-2-ynyloxy)phenyl]sulfonyl}amino)-N-hydroxy-5-[(2-phenylacetyl)amino]pentanamide;
N-[(4R)-4-({[4-(But-2-ynyloxy)phenyl]sulfonyl}amino)-5-(hydroxyamino)-5-oxopentyl]quinoline-3-carboxamide;
N-[(4R)-4-({[4-(But-2-ynyloxy)phenyl]sulfonyl}amino)-5-(hydroxyamino)-5-oxopentyl]thiophene-3-carboxamide;
(E)-N-[(4R)-4-({[4-(But-2-ynyloxy)phenyl]sulfonyl}amino)-5-(hydroxyamino)-5-oxopentyl]-3-phenylprop-2-enamide;
N-[(5R)-5-({[4-(But-2-ynyloxy)phenyl]sulfonyl}amino)-6-(hydroxyamino)-6-oxohexyl]-1H-benzimidazole-5-carboxamide;
N-[(5R)-5-({[4-(But-2-ynyloxy)phenyl]sulfonyl}amino)-6-(hydroxyamino)-6-oxohexyl]benzamide;
4-Bromo-N-[(5R)-5-({[4-(but-2-ynyloxy)phenyl]sulfonyl}amino)-6-(hydroxy-amino)-6-oxohexyl]benzamide;
N-[(5R)-5-({[4-(But-2-ynyloxy)phenyl]sulfonyl}amino)-6-(hydroxyamino)-6-oxohexyl]-3-chlorothiophene-2-carboxamide;
N-[(5R)-5-({[4-(But-2-ynyloxy)phenyl]sulfonyl}amino)-6-(hydroxyamino)-6-oxohexyl]4-chlorobenzamide;
N-[(5R)-5-({[4-(But-2-ynyloxy)phenyl]sulfonyl}amino)-6-(hydroxyamino)-6-oxohexyl]cycleohexanecarboxamide;
(2R)-2-({[4-(But-2-ynyloxy)phenyl]sulfonyl}amino)-6-{[2-(3,4-dichlorophenyl)-acetyl]amino}-N-hydroxyhexanamide;
N-[(5R)-5-({[4-(But-2-ynyloxy)phenyl]sulfonyl}amino)-6-(hydroxyamino)-6-oxohexyl]-2,5-dimethyl-3-furamide;
N-[(5R)-5-({[4-(But-2-ynyloxy)phenyl]sulfonyl}amino)-6-(hydroxyamino)-6-oxohexyl]-3,5-dimethylisoxazole-4-carboxamide;
(2R)-2-({[4-(But-2-ynyloxy)phenyl]sulfonyl}amino)-N-hydroxy-6-[(3-phenyl-propanoyl)amino]hexanamide;
N-[(5R)-5-({[4-(But-2-ynyloxy)phenyl]sulfonyl}amino)-6-(hydroxyamino)-6-oxohexyl]isonicotinamide;
N-[(5R)-5-({[4-(But-2-ynyloxy)phenyl]sulfonyl}amino)-6-(hydroxyamino)-6-oxohexyl]-2-methoxybenzamide;
N-[(5R)-5-({[4-(But-2-ynyloxy)phenyl]sulfonyl}amino)-6-(hydroxyamino)-6-oxohexyl]-4-methoxybenzamide;
(2R)-2-({[4-(But-2-ynyloxy)phenyl]sulfonyl}amino)-N-hydroxy-6-{[2-(4-nitrophenyl)acetyl]amino}hexanamide;
(2R)-2-({[4-(But-2-ynyloxy)phenyl]sulfonyl}amino)-N-hydroxy-6-[(2-phenylacetyl)amino]hexanamide;
N-[(5R)-5-({[4-(But-2-ynyloxy)phenyl]sulfonyl}amino)-6-(hydroxyamino)-6-oxohexyl]quinoline-3-carboxamide;
N-[(5R)-5-({[4-(But-2-ynyloxy)phenyl]sulfonyl}amino)-6-(hydroxyamino)-6-oxohexyl]thiophene-3-carboxamide;
(E)-N-[(5R)-5-({[4-(But-2-ynyloxy)phenyl]sulfonyl}amino)-6-(hydroxyamino)-6-oxohexyl]-3-phenylprop-2-enamide;
(Z)-N-[(4R)-4-({[4-(But-2-ynyloxy)phenyl]sulfonyl}amino)-5-(hydroxyamino)-5-oxopentyl]octadec-9-enamide;
N-[(4R)-4-({[4-(But-2-ynyloxy)phenyl]sulfonyl}amino)-5-(hydroxyamino)-5-oxopentyl]thiophene-2-carboxamide;
(2R)-2-({[4-(But-2-ynyloxy)phenyl]sulfonyl}amino)-5-{[(ethylamino)carbonyl]-amino}-N-hydroxypentanamide;
(2R)-5-[(Aminocarbonyl)amino]-2-({[4-(but-2-ynyloxy)phenyl]sulfonyl}amino)-N-hydroxypentanamide;
Octyl (4R)-4-({[4-(but-2-ynyloxy)phenyl]sulfonyl}amino)-5-(hydroxyamino)-5-oxopentylcarbamate;
4-Methoxyphenyl (4R)-4-({[4-(but-2-ynyloxy)phenyl]sulfonyl}amino)-5-(hydroxyamino)-5-oxopentylcarbamate;
(2R)-2-({[4-(But-2-ynyloxy)phenyl]sulfonyl}amino)-5-{[(diethylamino)-carbonyl]amino}-N-hydroxypentanamide;
(2R)-2-({[4-(But-2-ynyloxy)phenyl]sulfonyl}amino)-N-hydroxy-5-{[(methylamino)carbonyl]amino}pentanamide;
(2R)-2-({[4-(But-2-ynyloxy)phenyl]sulfonyl}amino)-N-hydroxy-5-{[(1-methyl-1H-imidazol-4-yl)sulfonyl]amino}pentanamide;
(2R)-2-({[4-(But-2-ynyloxy)phenyl]sulfonyl}amino)-N-hydroxy-5-[(2-morpholin-4-ylacetyl)amino]pentanamide;
(2R)-2-({[4-(But-2-ynyloxy)phenyl]sulfonyl}amino)-N-hydroxy-5-{[2-(4-methylpiperazin-1-yl)acetyl]amino}pentanamide; and
(2R)-5-{[2-(Benzylamino)acetyl]amino}-2-({[4-(but-2-ynyloxy)phenyl]sulfonyl}amino)-N-hydroxypentanamide.

Other preferred TACE inhibitor compounds of the present invention include acetylenic β-sulfonamido and phosphinic acid amide hydroxamic acids such as
(1R,2R)-2-[{[4-(2-Butynyloxy)phenyl]sulfonyl}(methyl)amino]-N-hydroxycyclohexanecarboxamide;
(1R,2R)-2-({[4-(2-Butynyloxy)phenyl]sulfonyl}amino)-N-hydroxycyclohexanecarboxamide;
3-({[4-(2-Butynyloxy)phenyl]sulfonyl}amino)-N-hydroxypropanamide;
3-({[4-(2-Butynyloxy)phenyl]sulfonyl}(methyl) amino)-N-hydroxypropanamide;
(1R,2S)-2-[{[4-(2-Butynyloxy)phenyl]sulfonyl}amino]-N-hydroxycyclopentanecarboxamide;
(1R,2S)-2-[{[4-(2-Butynyloxy)phenyl]sulfonyl}(methyl)amino] N-hydroxycyclopentanecarboxamide;
(Cis)-2-[{[4-(2-butynyloxy)phenyl]sulfonyl}amino)-N-hydroxycyclohexanecarboxamide;
(Cis)-2-[{[4-(2-butynyloxy)phenyl]sulfonyl}(methyl)amino]-N-hydroxycyclohexanecarboxamide;
(1R,2R,3S,4R)-(Cis)-3-({[4-(2-butynyloxy)phenyl]sulfonyl}amino)-N-hydroxybicyclo[2.2.1]heptane-2-carboxamide; and
(1R,2R,3S,4R)-(Cis)-3-({[4-(2-butynyloxy)phenyl]sulfonyl}(methyl)amino)-N-hydroxybicyclo[2.2.1]heptane-2-carboxamide.

Another group of preferred TACE inhibitor compounds include acetylenic aryl sulfonamide and phosphinic acid amide hydroxamic acids such as
5-Bromo-2-{[4-(4-cyclobutylamino-but-2-ynyloxy)-benzenesulfonyl]-methyl-amino}-N-hydroxy-3-methyl-benzamide;
5-Bromo-N-hydroxy-3-methyl-2-{methyl-[4-(4-methylamino-but-2-ynyloxy)-benzenesulfonyl]-amino}-benzamide;
5-Bromo-2-({4-[4-(3-dimethylamino-propylamino)-but-2-ynyloxy]-benzenesulfonyl}-methyl-amino)-N-hydroxy-3-methyl-benzamide;

5-Bromo-2-({4-[4-(2-dimethylamino-ethylamino)-but-2-ynyloxy]-benzenesulfonyl}-methyl-amino)-N-hydroxy-3-methyl-benzamide;
4-[(4-But-2-ynyloxy-benzenesulfonyl)-methyl-amino]-5-methyl-biphenyl-3-carboxylic acid hydroxyamide;
5-Bromo-N-hydroxy-3-methyl-2-[methyl-(4-prop-2-ynyloxy-benzenesulfonyl)-amino]-benzamide;
5-Bromo-N-hydroxy-3-methyl-2-[methyl-(4-pent-2-ynyloxy-benzenesulfonyl)-amino]-benzamide;
5-Bromo-2-[(4-hept-2-ynyloxy-benzenesulfonyl)-methyl-amino]-N-hydroxy-3-methyl-benzamide;
5-Bromo-2-[(4-hex-2-ynyloxy-benzenesulfonyl)-methyl-amino]-N-hydroxy-3-methyl-benzamide;
5-Bromo-N-hydroxy-2-{[4-(4-methoxy-but-2-ynyloxy)-benzenesulfonyl]-methyl-amino}-3-methyl-benzamide;
5-Bromo-N-hydroxy-3-methyl-2-{methyl-[4-(3-phenyl-prop-2-ynyloxy)-benzenesulfonyl]-amino}-benzamide;
5-Bromo-N-hydroxy-2-({4-[3-(3-methoxy-phenyl)-prop-2-ynyloxy]-benzenesulfonyl}-methyl-amino)-3-methyl-benzamide;
5-Bromo-N-hydroxy-2-({4-[3-(2-methoxy-phenyl)-prop-2-ynyloxy]-benzenesulfonyl}-methyl-amino)-3-methyl-benzamide;
5-Bromo-N-hydroxy-2-({4-[3-(4-methoxy-phenyl)-prop-2-ynyloxy]-benzenesulfonyl}-methyl-amino)-3-methyl-benzamide;
2-[(4-But-2-ynyloxy-benzenesulfonyl)-methyl-amino]-N-hydroxy-5-iodo-3-methyl-benzamide;
2-[Benzyl-(4-but-2-ynyloxy-benzenesulfonyl)-amino]-N-hydroxy-3,5-dimethyl-benzamide;
5-Bromo-N-hydroxy-3-methyl-2-{methyl-[4-(4-pyrrolidin-1-yl-but-2-ynyloxy)-benzenesulfonyl]-amino}-benzamide;
5-Bromo-2-{[4-(4-diethylamino-but-2-ynyloxy)-benzenesulfonyl]-methyl-amino-}-N-hydroxy-3-methyl-benzamide;
5-Bromo-2-[(4-but-2-ynyloxy-benzenesulfonyl)-(4-methyl-piperazin-1-ylmethyl)-amino]-N-hydroxy-3-methyl-benzamide;
5-Bromo-N-hydroxy-3-methyl-2-(methyl-{4-[4-(tetrahydro-pyran-2-yloxy)-but-2-ynyloxy]-benzenesulfonyl}-amino)-benzamide;
5-Bromo-N-hydroxy-2-{[4-(4-hydroxy-but-2-ynyloxy)-benzenesulfonyl]-methyl-amino}-3-methyl-benzamide; and
4-[(4-But-2-ynyloxy-benzenesulfonyl)-methyl-amino]-5-(4-methyl-piperazin-1-ylmethyl)-biphenyl-3-carboxylic acid hydroxyamide dihydrochloride salt.

Still another preferred group of TACE inhibitor compounds of the present invention includes acetylenic aryl sulfonamide thiols such as
4-But-2-ynyloxy-N-((1R)-2-mercapto-1-methyl-ethyl)-N-methylbenzene-sulfonamide;
(2R)-2-{{[4-(2-Butynyloxy)phenyl]sulfonyl}[2-(4-morpholinyl)ethyl]amino}-3-sulfanylpropanamide; and
4-(2-Butynyloxy)-N-[(1R)-1-methyl-2-sulfanylethyl]-N-[2-(4-morpholinyl)ethyl]benzenesulfonamide.

Yet another group of preferred TACE inhibitor compounds of the present invention includes acetylenic aryl and heteroaryl sulfonamide and phosphinic acid amide hydroxamic acids such as (3-[methyl-(4-but-2-ynyloxy-benzenesulfonyl)-amino]-N-hydroxy-2,6-dimethoxy-isonicotinamide and 3-(4-But-2-ynyloxy-benzenesulfonylamino)-N-hydroxy-2,6-dimethoxy-isonicotinamide.

Other preferred TACE inhibitor compounds of the present invention include alkynyl containing hydroxamic acid compounds such as
2-(4-But-2-ynyloxy-benzenesulfonyl)-N-hydroxy-2-methyl-3-pyridin-3-yl-propionamide;
2-(4-But-2-ynyloxy-phenylsulfanyl)-N-hydroxy-propionamide;
2-(4-But-2-ynyloxy-benzesulfonyl)-N-hydroxy-2-methyl-3-[4-(2-piperidin-1-yl-ethoxy)-phenyl]-propionamide;
3-Biphenyl-4-yl-2-(4-but-2-ynyloxy-benzenesulfonyl)-N-hydroxy-2-methyl-propionamide;
2-(4-But-2-ynyloxy-phenysulfanyl)-octanoic acid hydroxamide;
2-(But-2-ynyloxy-benzenesulfonyl)-octanoic acid hydroxamide;
2[(R)-(4-Butyl-2-ynyloxy)-sulfinyl-N-hydroxyoctanamide;
2[(S)-(4-Butyl-2-ynyloxy)-sulfinyl-N-hydroxyoctanamide;
3-(4-But-2-ynyloxy-phenoxy)-N-hydroxy-propionamide
4-(4-But-2-ynyloxy-phenoxy)-N-hydroxy-butyramide;
2-(4-But-2-ynyloxy-phenoxy)-N-hydroxy-acetamide;
4-(4-But-2-ynyloxy-phenyl)-N-hydroxy-butyramide;
Quinoline-2-carboxylic acid [5-(4-but-2-ynyloxy-phenylsulfanyl)-5-hydroxycarbamoyl-pentyl]-amide;
2-(4-But-2-ynyloxy-phenylsulfanyl)-6-[2-(1,3-dioxo-1,3-dihydro-isoindol-2-yl)-acetylamino]-hexanoic acid hydroxyamide;
N-[5-(4-But-2-ynyloxy-phenylsulfanyl)-5-hydroxycarbamoyl-pentyl]-2-phenethyl-benzamide;
2-(4-But-2-ynyloxy-phenylsulfanyl)-6-[2-(3,4-dichloro-phenyl)-acetylamino]-hexanoic acid hydroxyamide;
Quinoline-3-carboxylic acid [5-(4-but-2-ynyloxy-phenylsulfanyl)-5-hydroxycarbamoyl-pentyl]-amide;
2-(4-But-2-ynyloxy-phenylsulfanyl)-6-(4-thiophen-2-yl-butyrylamino)-hexanoic acid hydroxyamide;
9H-Xanthene-9-carboxylic acid [5-(4-but-2-ynyloxy-phenylsulfanyl)-5-hydroxycarbamoyl-pentyl]-amide;
2-(4-But-2-ynyloxy-phenylsulfanyl)-6-diphenylacetylamino-hexanoic acid hydroxyamide;
Isoquinoline-1-carboxylic acid [5-(4-but-2-ynyloxy-phenylsulfanyl)-5-hydroxycarbamoyl-pentyl]-amide;
6-(2-Benzo[b]thiophen-3-yl-acetylamino)-2-(4-but-2-ynyloxy-phenyl-sulfanyl)-hexanoic acid hydroxyamide;
Quinoline-2-carboxylic acid [5-(4-but-2-ynyloxy-benzenesulfinyl)-5-hydroxycarbamoyl-pentyl]-amide;
2-(4-But-2-ynyloxy-benzenesulfinyl)-6-[2-(1,3-dioxo-1,3-dihydro-isoindol-2-yl)-acetylamino]-hexanoic acid hydroxyamide;
N-[5-(4-But-2-ynyloxy-benzenesulfinyl)-5-hydroxycarbamoyl-pentyl]-2-phenethyl-benzamide;
2-(4-But-2-ynyloxy-benzenesulfinyl)-6-[2-(3,4-dichloro-phenyl)-acetylamino]-hexanoic acid hydroxyamide;
Quinoline-3-carboxylic acid [5-(4-but-2-ynyloxy-benzenesulfinyl)-5-hydroxycarbamoyl-pentyl]-amide;
2-(4-But-2-ynyloxy-benzenesulfinyl)-6-(4-thiophen-2-yl-butyrylamino)-hexanoic acid hydroxyamide;
9H-Xanthene-9-carboxylic acid [5-(4-but-2-ynyloxy-benzenesulfinyl)-5-hydroxycarbamoyl-pentyl]-amide;
2-(4-But-2-ynyloxy-benzenesulfinyl)-6-diphenylacetylamino-hexanoic acid hydroxyamide;
Isoquinoline-1-carboxylic acid [5-(4-but-2-ynyloxy-benzenesulfinyl)-5-hydroxycarbamoyl-pentyl]-amide;
6-(2-Benzo[b]thiophen-3-yl-acetylamino)-2-(4-but-2-ynyloxy-benzene-sulfinyl)-hexanoic acid hydroxyamide;
2-(4-But-2-ynyloxy-benzenesulfinyl)-6-(2-1H-indol-3-yl-acetylamino)-hexanoic acid hydroxyamide;
Quinoline-2-carboxylic acid [5-(4-but-2-ynyloxy-benzenesulfonyl)-5-hydroxycarbamoyl-pentyl]-amide;

2-(4-But-2-ynyloxy-benzenesulfonyl)-6-[2-(1,3-dioxo-1,3-dihydro-isoindol-2-yl)-acetylamino]-hexanoic acid hydroxyamide;

N-[5-(4-But-2-ynyloxy-benzenesulfonyl)-5-hydroxycarbamoyl-pentyl]-2-phenethyl-benzamide;

2-(4-But-2-ynyloxy-benzenesulfonyl)-6-[2-(3,4-dichloro-phenyl)-acetyl-amino]-hexanoic acid hydroxyamide;

Quinoline-3-carboxylic acid [5-(4-but-2-ynyloxy-benzenesulfonyl)-5-5-hydroxycarbamoyl-pentyl]-amide;

9H-Xanthene-9-carboxylic acid [5-(4-but-2-ynyloxy-benzenesulfonyl)-5-hydroxycarbamoyl-pentyl]-amide;

2-(4-But-2-ynyloxy-benzenesulfonyl)-6-diphenylacetylaminohexanoic acid hydroxyamide;

Isoquinoline-1-carboxylic acid [5-(4-but-2-ynyloxy-benzenesulfonyl)-5-hydroxycarbamoyl-pentyl]-amide;

6-(2-Benzo[b]thiophen-3-yl-acetylamino)-2-(4-but-2-ynyloxy-benzene-sulfonyl)-hexanoic acid hydroxyamide;

Quinoline-2-carboxylic acid {[5-(4-but-2-ynyloxy-phenylsulfanyl)-5-hydroxycarbamoyl-pentylcarbamoyl]-methyl}-amide;

2-(4-But-2-ynyloxy-phenylsulfanyl)-6-{2-[2-(1,3-dioxo-1,3-dihydro-isoindol-2-yl)-acetylamino]-acetylamino}hexanoic acid hydroxyamide;

N-{[5-(4-But-2-ynyloxy-phenylsulfanyl)-5-hydroxycarbamoyl-pentyl-carbamoyl]-methyl}-2-phenethyl-benzamide;

2-(4-But-2-ynyloxy-phenylsulfanyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-phenylsulfanyl)-5-hydroxycarbamoyl-pentylcarbamoyl]-methyl}-amide;

9H-Xanthene-9-carboxylic acid {[5-(4-but-2-ynyloxy-phenylsulfanyl)-5-hydroxycarbamoyl-pentylcarbamoyl]-methyl}amide;

2-(4-But-2-ynyloxy-phenylsulfanyl)-6-(2-diphenylacetylamino-acetylamino)-hexanoic acid hydroxyamide;

Isoquinoline-1-carboxylic acid {[5-(4-but-2-ynyloxy-phenylsulfanyl)-5-hydroxycarbamoyl-pentylcarbamoyl]-methyl}-amide;

1-Methyl-1H-pyrrole-2-carboxylic acid {[5-(4-but-2-ynyloxy-phenyl-sulfanyl)-5-hydroxycarbamoyl-pentylcarbamoyl]-methyl}-amide;

6-[2-(2-Benzo[b]thiophen-3-yl-acetylamino)-acetylamino]-2-(4-but-2-ynyloxy-phenylsulfanyl hexanoic acid hydroxyamide;

Quinoline-2-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-{2-[2-(1,3-dioxo-1,3-dihydro-isoindol-2-yl)-acetylamino]-acetylamino}-hexanoic acid hydroxyamide;

N-{[5-(4-But-2-ynyloxy-benzenesulfinyl)-5-hydroxycarbamoyl-pentyl-carbamoyl]-methyl}-2-phenethyl-benzamide;

2-(4-But-2-ynyloxy-benzenesulfinyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-benzenesulfinyl)-5-hydroxycarbamoyl-pentylcarbamoyl]-methyl}amide;

2-(4-But-2-ynyloxy-benzenesulfinyl)-6-[2-(4-thiophen-2-yl-butyrylamino)-acetylamino]-hexanoic acid hydroxyamide;

9H-Xanthene-9-carboxylic acid {[5-(4-but-2-ynyloxy-benzenesulfinyl)-5-hydroxycarbamoyl-pentylcarbamoyl]-methyl}-amide;

2-(4-But-2-ynyloxy-benzenesulfinyl)-6-(2-diphenylacetylamino-acetylamino)-hexanoic acid hydroxyamide;

1-Methyl-1H-pyrrole-2-carboxylic acid {[5-(4-but-2-ynyloxy-benzene-sulfinyl)-5-hydroxycarbamoyl-pentylcarbamoyl]-methyl}-amide;

2-(4-But-2-ynyloxy-benzenesulfonyl)-6-{2-[2-(1,3-dioxo-1,3-dihydro-isoindol-2-yl)-acetylamino]-acetylamino}-hexanoic acid hydroxyamide;

N-{[5-(4-But-2-ynyloxy-benzenesulfonyl)-5-hydroxycarbamoyl-pentylcarbamoyl]-methyl}-2-phenethyl-benzamide;

2-(4-But-2-ynyloxy-benzenesulfonyl)-6-{2-[2-(3,4-dichloro-phenyl)-acetylamino]-acetylamino}-hexanoic acid hydroxyamide;

Quinoline-3-carboxylic acid {[5-(4-but-2-ynyloxy-benzenesulfonyl)-5-hydroxycarbamoyl-pentylcarbamoyl]-methyl}amide;

9H-Xanthene-9-carboxylic acid {[5-(4-but-2-ynyloxy-benzenesulfonyl)-5-hydroxycarbamoyl-pentylcarbamoyl]-methyl}-amide;

2-(4-But-2-ynyloxy-benzenesulfonyl)-6-(2-diphenylacetylamino-acetylamino)-hexanoic acid hydroxyamide;

Isoquinoline-1-carboxylic acid {[5-(4-but-2-ynyloxy-benzenesulfonyl)-5-hydroxycarbamoyl-pentylcarbamoyl]-methyl}-amide;

6-[2-(2-Benzo[b]thiophen-3-yl-acetylamino)-acetylamino]-2-(4-but-2-ynyloxy benzenesulfonyl hexanoic acid hydroxyamide;

2-(4-But-2-ynyloxy-benzenesulfonyl)-6-[2-(2-1H-2-indol-3-yl-acetylamino)-acetylamino]-hexanoic acid hydroxyamide;

2-{[4-(2-butynyloxy)phenyl]sulfonyl}-N-hydroxy-4-{4-[2-(1-piperidinyl)ethoxy phenyl}butanamide;

2-{[4-(2-butynyloxy)phenyl]sulfonyl}-7-cyano-N-hydroxy heptanamide;

2-{[4-(2-butynyloxy)phenyl]sulfanyl}-2-cyclohexyl-N-hydroxyacetamide;

2-{[4-(2-butynyloxy)phenyl]sulfinyl}-2-cyclohexyl-N-hydroxyacetamide;

2-{4-(2-butynyloxy)phenyl]suffonyl}-2-cyclohexyl-N-hydroxyacetamide;

2-{[4-(2-butynyloxy)phenyl]sulfanyl}-N-hydroxy-2-(4-methoxyphenyl)acetamide;

(2R)-2-{[4-(2-butynyloxy)phenyl]sulfinyl}-N-hydroxy-2-(4-methoxyphenyl)ethanamide;

(2S)-2{[4-(2-butynyloxy)phenyl]sulfinyl}-N-hydroxy-2-(4-methoxyphenyl)ethanamide;

2-{[4-(2-butynyloxy)phenyl]sulfonyl}-N-hydroxy-2-(4-methoxyphenyl)acetamide;

2-[4-(2-butynyloxy)phenyl]sulfanyl)-2-(4-chlorophenyl)-N-hydroxyacetamide;

2-[4-(2-butynyloxy)phenyl]sulfinyl}-2-(4-chlorophenyl)N-hydroxyacetamide;

2-{[4-(2-butynyloxy)phenyl]sulfonyl-2-(4-chlorophenyl)-N-hydroxy-acetamide;

2-{[4-(2-butynyloxy)phenyl]sulfanyl}-2-(3-chlorophenyl)-N-hydroxyacetamide;

2-{[4-(2-butynyloxy)phenyl]sulfonyl}-2-(3-chlorophenyl)-N-hydroxyacetamide;

2-(4-bromophenyl)-2-{[4-(2-butynyloxy)phenyl]sulfanyl-N-hydroxyacetamide;

(2S)-2-(4-bromophenyl)-2-{[4-(2-butynyloxy)phenyl]sulfinyl-N-hydroxy-acetamide;

(2R)-2-(4-bromophenyl)-2-{[4-(2-butynyloxy)phenyl]sulfinyl-N-hydroxy-acetamide;

2-(4-bromophenyl)-2-{[4-(2-butynyloxy)phenyl]sulfonyl-N-hydroxy-acetamide;

2-{[4-(2-butynyloxy)phenyl]sulfanyl]-N-hydroxy-2-[4-(2-thienyl)phenyl]-acetamide;

(2R)-2-[4-(2-butynyloxy)phenyl]sulfinyl}-N-hydroxy-2-[4-(2-thienyl)-phenyl]ethanamide;

2-{[4-(2-butynyloxy)phenyl]sulfonyl}-N-hydroxy-2-[4-(2-thienyl)-phenyl]acetamide;

2-[4-(2-Butynyloxy)phenyl]sulfanyl}-N-hydroxy-2-(1-napthyl)acetamide;

2-[4-(2-Butynyloxy)phenyl]sulfinyl}-N-hydroxy-2-(1-napthyl)acetamide;

2-{[4-(2-Butynyloxy)phenyl]sulfonyl}-N-hydroxy-2-(1-napthyl)acetamide;

2-{[4-(2-Butynyloxy)phenyl]sulfanyl]-2-(4-fluorophenyl)-N-hydroxy-2-(1-napthyl)acetamide;

2-{[4-(2-butynyloxy)phenyl]sulfinyl-2-(4-fluorophenyl)-N-hydroxy acetamide;

2-{[4-(2-butynyloxy)phenyl]sulfonyl-2-(4-fluorophenyl)-N-hydroxyacetamide;

2-(2-methoxyphenyl)-2-{[4-(2-butynyloxy)phenyl]sulfanyl-N-hydroxy-acetamide;

2-(2-methoxyphenyl)-2-{[4-(2-butynyloxy)phenyl]sulfinyl}-N-hydroxy-acetamide;

2-{[4-(2-butynyloxy)phenyl]sulfanyl-N-hydroxy-2-(4-ethoxyphenyl) acetamide;

2-{[4-(2-Butynyloxy)phenyl]sulfinyl-N-hydroxy-2-(4-ethoxyphenyl) acetamide;

2-[4-(2-butynyloxy)phenyl]sulfonyl-2-(4-chlorophenyl)-N-hydroxyacetamide;

2-([4-(2-Butynyloxy)phenyl]sulfanyl-N-hydroxy-2-(3-bromophenyl)acetamide;

(2R)-2-{[4-(2-butynyloxy)phenyl]sulfinyl-N-hydroxy-2-(3-bromophenyl)acetamide;

(2S)-2-{[4-(2-butynyloxy)phenyl]sulfinyl-N-hydroxy-2-(3-bromophenyl)acetamide;

2-{[4-(2-Butynyloxy)phenyl]sulfonyl)-2-(3-bromophenyl)-N-hydroxyacetamide;

2-[4-(2-Butynyloxy)phenyl]sulfanyl}-2-isopropyl-N-hydroxyacetamide;

R-2-[4-(2-butynyloxy)phenyl]sulfinyl}-2-isopropyl-N-hydroxyacetamide;

S-2-{[4-(2-butynyloxy)phenyl]sulfinyl}2-isopropyl-N-hydroxyacetamide;

2-{[4-(2-butynyloxy)phenyl]sulfonyl}-2-isopropyl-N-hydroxyacetamide;

2-[4-(2-Butynyloxy)phenyl]sulfanyl)-2-phenyl-N-hydroxy-acetamide;

R-2-[4-(2-butynyloxy)phenyl]sulfinyl}-2-phenyl-N-hydroxyacetamide;

S-2-{[4-(2-butynyloxy)phenyl]sulfinyl}-2-phenyl-N-hydroxyacetamide;

2-{[4-(2-Butynyloxy)phenyl]sulfanyl}-2-(2-naphthyl)-N-hydroxyacetamide;

2-{[4-(2-butynyloxy)phenyl]sulfinyl}2-(2-naphthyl)-N-hydroxyacetamide;

2-{[4-(2-butynyloxy)phenyl]sulfonyl)-2-(2-naphthyl)-N-hydroxyacetamide;

Tert-butyl-4-[11{[4-(2-butynyloxy)phenyl]sulfonyl}-2-(hydroxyamino)-2-oxoethyl]-1-piperidine carboxylate;

2-{[4-(2-butynyloxy)phenyl]sulfonyl}N-hydroxy-2-(4-piperidinyl)acetamide;

2-[4-(2-butynyloxy)phenyl]sulfonyl}-N-hydroxy-2-[1-(4-methoxybenzyl)-4-piperidinyl]acetamide;

2-(1-benzoyl-4-piperidinyl)-2-{[4-(2-butynyloxy)phenyl-sulfony-}-N-hydroxy-acetamide;

2-(1-acetyl-4-piperidinyl)-2-[4-(2-butynyloxy)phenyl]sulfonyl-N-hydroxy-acetamide;

2-{[4-(2-Butynyloxy)phenyl]sulfonyl}-N-hydroxy-2-tetrahydro-2H-pyran-4yl-acetamide;

2-{[4-(2-Butynyloxy)phenyl]sulfonyl)-N-hydroxy-2-tetrahydro-2H-thiopyran-4yl-acetamide;

2-[4-(2-Butynyloxy)phenyl]sulfonyl}-N-hydroxy-2-(1-oxidotetrahydro-2H-thiopyran-4yl) acetamide; and 2-{[4-(2-Butynyloxy)phenyl]sulfonyl}-N-hydroxy-2-(1,1-dioxidotetrahydro-2H-thiopyran-4yl) acetamide.

Other preferred TACE inhibitor compounds of the present invention include carboxamides and hydroxamides such as 1-(4-Bromo-benzyl)-4-(4-but-2-ynyxoy-benzenesulfonyl)-piperdine-4-carboxylic acid hydroxyamide;

4-(4-But-2-ynyloxy-benzenesulfonyl)-1-(4-methoxy-benzyl)-piperdine-4-carboxylic acid hydroxyamide;

4-(4-But-2-ynyloxy-benzenesulfonyl)-1-(4-chloro-benzyl)-piperdine-4-carboxylic acid hydroxyamide;

1-Benzyl-4-(4-but-2-ynyloxy-benzenesulfonyl)-piperdine-4-carboxylic acid hydroxamide;

1-(4-Bromo-benzyl)-4-(4-pent-2-ynyloxy-benzenesulfonyl)-piperdine-4-carboxylic acid hydroxyamide;

1-(4-Bromo-benzyl)-4-(4-oct-2-ynyloxy-benzenesulfonyl)-piperdine-4-carboxyiic acid hydroxyamide;

4-(4-But-2-ynyloxy-benzenesulfonyl)-1-(4-fluoro-benzyl)-piperdine-4-carboxylic acid hydroxyamide;

4-(4-But-2-ynyloxy-benzenesulfonyl)-1-(4-cyano-benzyl)-piperidine-4-carboxylic acid hydroxyamide;

4-(4-But-2-ynyloxy-benzenesulfonyl)-1-(4-methyl-benzyl)-piperidine-4-carboxylic acid hydroxyamide;

4-(4-But-2-ynyloxy-benzenesulfonyl)-1-(3,4-dichloro-benzyl)-piperidine-4-carboxylic acid hydroxyamide;

1-(4-Bromo-benzyl)-4-(4-prop-2-ynyloxy-benzenesulfonyl)-piperdine-4-carboxylic acid hydroxyamide;

1-(4-Bromo-benzyl)-4-[4-(4-piperdin-4-yl-but-2-ynyloxy)-benzenesulfonyl]-piperidine-4-carboxylic acid hydroxyamide;

1-(4-Bromo-benzyl)-4-[4-(4-morpholin-4-yl-but-2-ynyloxy)-benzene-sulfonyl]-piperdine-4-carboxylic acid hydroxyamide;

4-(4-But-2-ynyloxy-phenylsulfanyl)-4-hydroxycarbamoyl-piperidine-1-carboxylic acid tert-butyl ester;

4-(4-But-2-ynyloxy-phenylsulfanyl)-piperidine-4-carboxylic acid hydroxyamide 1-(4-Bromo-benzyl)-4-(4-but-2-ynyloxy-phenylsulfanyl)-piperidine-4-carboxylic acid hydroxyamide;

4-(4-But-2-ynyloxy-phenylsulfanylmethyl)-tetrahydro-pyran-4-carboxylic acid hydroxyamide;

4-(4-But-2-ynyloxy-benzenesulfonylmethyl)-tetrahydro-pyran-4-carboxylic acid hydroxyamide;

4-(4-But-2-ynyloxy-benzenesulfinylmethyl)-tetrahydro-pyran-4-carboxylic acid hydroxyamide;

4-{[4-(2-butynyloxy)phenyl]sulfonyl}-N-hydroxytetrahydro-2H-pyran-4-carboxamide;

1-benzyl-4-[3-(2-butynyloxy)phenyl]sulfonyl}-N-hydroxy-4-piperdine carboxamide;

4-{[4-(2-butynyloxy)phenyl]suffonyl}-N-hydroxy-1-isopropyl-4-piperidine carboxamide;

4-{[4-(2-butynyloxy)phenyl]sulfonyl}-N-hydroxy-1-(3-pyddinylmethyl)-4-piperidine carboxamide;

3-{[4-(2-Butynyloxy)phenyl]sulfonyl}1-ethyl-N-hydroxy-3-piperidine-carboxamide;

3-{[4-(2-butynyloxy)phenyl]sulfonyl)-1-(4-chlorobenzyl)-N-hydroxy-3-piperidinecarboxamide;

4{[4-(2-Butynyloxy)phenyl]sulfonyl}-1-[4-(2-piperidin-1-yl-ethoxy)-benzyl]-piperidine-4-carboxylic acid hydroxyamide;

4-{[4-(2-Butynyloxy)phenyl]sulfonyl]-1-(3-pentanyl)-piperidine-4-carboxylic acid hydroxyamide;

1-(4-Methoxy-benzyl)-4-(4-prop-2-ynyloxy-benzenesulfonyl)-piperidine-4-carboxylic acid hydroxyamide;

1-(4-Chloro-benzyl)-4-(4-prop-2-ynyloxy-benzenesulfonyl)-piperidine-4-carboxylic acid hydroxyamide;

tert-butyl-4-({[4-(2-butynyloxy)phenyl-1-sulfanyl methyl)-4-[(hydroxyamino)-carbonyl]-1-piperidinecarboxylate;

4-({[4-(But-2-ynyloxy)phenyl]thio}methyl)-N-hydroxypiperidine-4-carboxamide;

tert-Butyl-4-(([4-(2-butynyloxy)phenyl]sulfinylmethyl)-4-[(hydroxyamino)-carbonyl]-1-piperidinecarboxylate;

4-[[[4-(2-Butynyloxy)phenyl]sulfinyl]methyl]-N-hydroxy-4-piperidine-carboxamide;

tert-Butyl-4-({[4-(but-2-ynyloxy)phenyl]sulfonyl}-methyl)-4-[(hydroxyamino)-carbonyl]piperidine-1-carboxylate;

tert-butyl-4-({[4-(2-butynyloxy)phenyl]sulfonyl}methyl)-4-(hydroxyamino)-carbonyl]-1-piperidinecarboxylate;

1-Acetyl-4-[[[4-(2-butynyloxy)phenyl]sulfonyl]methyl]-N-hydroxy-4-piperidinecarboxamide;

1-(2-Butynyl)-4-({[4-(2-butynyloxy)phenyl]sulfonyl}methyl)-N-hydroxy-4-piperidinecarboxamide hydrochloride;

N-1-(tert-Butyl)-4-({[4-(2-butynyloxy)phenyl]sulfonyl}methyl)-N-4-hydroxy-1,4-[4-(2-butynyloxy)phenyl]sulfonyl}methyl)-N-hydroxy-1,4-l]sulfonyl}-methyl)-N-hydroxy-1,4-piperidinedicarboxamide;

Methyl 4-({[4-(2-butynyloxy)phenyl]sulfonyl}methyl)-4-[(hydroxyamino)-carbonyl]-1-piperidinecarboxylate;

Benzyl 4-({[4-(2-butynyloxy)phenyl]sulfonylmethyl)-4-[(hydroxyamino)-carbonyl]-1-piperidinecarboxylate;

1-Benzyl-4-({[4-(2-butynyloxy)phenyl]sulfonyl}methyl)-N-hydroxy-4-butynyloxy)phenyl]sulfonyl}methyl)-N-hydroxy-4-piperidinecarboxamide;

4-({[4-(2-Butynyloxy)phenyl]sulfonyl}methyl)-N-hydroxy-1-[(2,2,5-trimethyl-1,3-dioxan-5-yl)carbonyl]4-piperidinecarboxamide;

4-({[4-(2-Butynyloxy)phenyl]sulfonylmethyl)-N-hydroxy-1-[3-hydroxy-2-(hydroxymethyl)-2-methylpropanoyl]-4-piperidinecarboxamide;

1-[Amino(imino)methyl]-4-({[4-(2-butynyloxy)phenyl]sulfonyl}methyl)-N-hydroxy-4-l]4-({[4-(2-butynyloxy)phenyl]sulfonylmethyl)-N-hydroxy-4-oxy)phenyl]sulfonyl}methyl)-N-hydroxy-4-piperidinecarboxamide;

4-({[4-(2-Butynyloxy)phenyl]sulfonyl}methyl)-N-hydroxy-1-(4-hydroxy-2-butynyl)-phenyl]sulfonyl}methyl)-N-hydroxy-1-(4-hydroxy-2-butynyl)-4-piperidinecarboxamide;

4-({[4-(But-2-ynyloxy)phenyl]sulfonyl}methyl)-1-ethyl-N-hydroxypiperidine-4-carboxamide triflouroacetic acid salt;

2-chloro-5-(chloromethyl) thiophene-4-({[4-(But-2-ynyloxy)phenyl]-sulfonyl}-methyl)-1-[(5-chlorothien-2-yl)methyl]-N-hydroxypiperidine-4-carboxamide triflouroacetic acid salt;

4-({[4-(But-2-ynyloxy)phenyl]sulfonyl}methyl)-N-hydroxy-1-(pyridin-4-ylmethyl)piperidine-4-carboxamide triflouroacetic acid salt;

4-({[4-(But-2-ynyloxy)phenyl]sulfonyl}methyl)-N-hydroxy-1-(pyridin-3 ylcarbonyl)piperidine-4-carboxamide triflouroacetic acid salt;

1-Benzoyl-4-({[4-(but-2-ynyloxy)phenyl]sulfonylmethyl)-N-hydroxy-piperidine-4-carboxamide;

4-({[4-(But-2-ynyloxy)phenyl]sulfonyl}methyl)-N-hydroxy-1-(thien-2-ylcarbonyl) piperidine-4-carboxamide;

4-({[4-(But-2-ynyloxy)phenyl]sulfonyl}methyl)-N-1 ethyl-N-4-hydroxy-piperidine-1,4-dicarboxamide;

4-({([4-(But-2-ynyloxy)phenyl]sulfonyl}methyl)-N-4-hydroxy-N-1-phenyl-piperidine-1,4-dicarboxamide;

4-({[4-(But-2-ynyloxy)phenyl]sulfonyl}methyl)-N-1-,N-1-diethyl-N-4-hydroxypiperidine-1,4-dicarboxamide;

4-({[4-(But-2-ynyloxy)phenyl]sulfonyl}methyl)-N-hydroxy-1-(morpholin-4-ylcarbonyl)piperidine-4-carboxamide;

4-({[4-(But-2-ynyloxy)phenyl]sulfonyl}methyl)-N-4-hydroxy-N-1-methyl-N-1-phenylpiperidine-1,4-dicarboxamide;

Octyl-4-({[4-(but-2-ynyloxy)phenyl]sulfonyl}methyl)-4-[(hydroxyamino)-carbonyl]piperidine-1-carboxylate;

4-Methoxyphenyl-4-({[4-(but-2-ynyloxy)phenyl]sulfonyl]methyl)-4-[(hydroxy-amino)carbonyl]piperidine-1-carboxylate;

4-({[4-(But-2-ynyloxy)phenyl]sulfonyl}methyl)-N-hydroxy-1-(phenylsulfonyl)piperidine-4-carboxamide;

4-({[4-(But-2-ynyloxy)phenyl]sulfonyl}methyl)-N-hydroxy-1-[(1-methyl-1H-imidazol-4-yl)sulfonyl]piperidine-4-carboxamide;

1-[2-(Benzylamino)acetyl]4-({[4-(but-2-ynyloxy)phenyl]-sulfony}methyl)-N-hydroxypiperldine-4-carboxamide;

4-({[4-(But-2-ynyloxy)phenyl]sulfonyl}methyl)-N-hydroxy-1-(2-morpholin-4-ylacetyl)piperidine-4-carboxamide;

4-({[4-(But-2-ynyloxy)phenyl]sulfonyl}methyl)-N-hydroxy-1-[2-(4-methyl-piperazin-1-yl)acetyl]piperidine-4-carboxamide;

1-Acetyl-4-(4-but-2-ynyloxybenzenesulfonyl)piperidine-4-carboxylic acid hydroxamide;

1-Benzoyl-4-(4-but-2-ynyloxybenzenesulfonyl)piperidine-4-carboxylic acid hydroxamide;

1-(4-Methoxybenzoyl)-4-(4-but-2-ynyloxy benzenesulfonyl)piperidine-4-carboxylic acid hydroxamide;

4-(4-But-2-ynyloxybenzenesulfonyl)-N-hydroxy-1-(pyrrolidine-1-carbonyl)-4-piperidinecarboxamide;

Ethyl 4-(4-but-2-ynyloxybenzenesulfonyl)-4-[(hydroxyamino)carbonyl]-1-piperidinecarboxylate;

4-(4-But-2-ynyloxybenzenesulfonyl)-N-hydroxy-1-[(trifluoromethyl)sulfonyl]-4-piperidinecarboxamide;

4-(4-But-2-ynyloxybenzenesulfonyl)-N-hydroxy-1-(3-pyridinylcarbonyl)-4-piperidinecarboxamide;

4-(4-but-2-ynyloxybenzenesulfonyl)-N-hydroxy-1-(2-thienylcarbonyl)-4-piperidinecarboxamide;

4-(4-but-2-ynyloxybenzenesulfonyl)-N-hydroxy-1-[(4-methoxyphenyl)-sulfonyl]-4-piperidinecarboxamide;

4-(4-but-2-ynyloxybenzenesulfonyl)-N-hydroxy-1-[(2,2,5-trimethyl-1,3-dioxan-5-yl)carbonyl]-4-piperidinecarboxamide;

Tert-butyl-4-{[4-(2-butynyloxy)phenyl]sulfonyl}-4-[(hydroxyamino)carbonyl)-1-piperidinecarboxalate;

4-{[4-(2-butynyloxy)phenyl]sulfonyl}-N-hydroxy-4-piperidinecarboxamide hydrochloride;

Methyl ({4-{[4-(2-butynyloxy)phenyl]sulfonyl}4-[(hydroxyamino)carbonyl]-1-piperidinyl}methyl)benzoate hydrochloride;

4-({4-{[4-(2-butynyloxy)phenyl]sulfonyl}4-[(hydroxyamino)carbonyl]-1-piperidinyl}methyl)benzoic acid hydrochloride;

1-[4-(Aminocarbonyl)benzyl]4-([4-(2-butynyloxy)phenyl] sulfonyl}N-hydroxy-4-piperidinecarboxamide hydrochloride;

Tert-butyl 4-{[4-(but-2-ynyloxy)phenyl]sulfinyl}4-[(hydroxyamino)-carbonyl]piperidine-1-carboxalate;

4-(4-(But-2-ynyloxy-benzenesulfinyl)-piperidine-4-carboxylic acid hydroxamide hydrochloride; and 1-(4-Bromo-benzyl)-4-(4-But-2-ynyloxy-benzenesulfinyl)-piperidine-4-carboxylic acid hydroxamide hydrochloride;

In the present invention "an effective amount" of the EGF receptor kinase inhibitor compound will vary with inter alia the individual patient and the severity of the disease, however generally it will be at least about 5 mg/kg. A preferred range is about 10 to 50 mg/kg.

In the present invention "an effective amount" of the TACE inhibitor compound will vary with a variety of factors including the individual patient and the severity of the disease. Typically the effective amount will be at least about 5 mg/kg. A preferred range is about 20 to 40 mg/kg.

The dosing schedule of the drug(s) may be from once to several times per day or may be less frequent. Preferably the dosing will be less frequent, for example dosing every other day, every third day or once a week.

In the present invention, the terms TACE inhibitor, TACE inhibitor compound, EGF receptor kinase inhibitor, and EGF receptor kinase inhibitor compound include all optical isomers and diastereomers as well as pharmaceutically acceptable salts.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

An effective amount of the compound[s]of the invention are provided to the patient. The compounds may be provided orally, in liquid or solid form, or by injection. In addition the compound may be provided to the patient via a pro-drug route wherein the patient actually converts in vivo a substance given to him or her to one or more of the TACE inhibitors or EGF receptor kinase inhibitors of the present invention.

The following examples are merely illustrative of the present invention. The invention is not to be limited thereby.

EXAMPLE 1

The bpk Model of ARPKD

This model arose from a spontaneous mutation in a colony of BALB/C mice. Affected animals have many similarities to the human disease including collecting tubule (CT) cysts and biliary ectasia and fibrosis. The kidney disease has a consistent and severe phenotype. Mice homozygous for the bpk mutation have microscopic evidence of cyst formation at birth. Proximal tubule (PT) cysts are present at birth, which are gradually replaced by CT cysts as the disease progresses. Cyst expansion and kidney fibrosis result in death due to renal failure at 24-28 days. Heterozygotes show no phenotypic abnormalities and are identified by their ability to breed affected offspring. Unaffected (noncystic) littermates of cystic bpk mice are either wild-type or heterozygous at the bpk locus.

TGF-α Expression in bpk Mice

Kidneys were obtained from cystic bpk mice and noncystic littermates at postnatal days 7, 14 and 21. Immunohistology was performed formaldehyde-fixed specimens embedded in plastic [See Sweeney W E et al: Treatment of polycystic kidney disease with a novel tyrosine kinase inhibitor, *Kidney Int.* 57:3340, 2000.]Primary antibody was a polyclonal anti-TGF-α (Chemicon, Temecula, Calif.) directed against recombinant 6 kD human TGF-α and reactive to mouse. Tubular localization of antibody staining was assessed by staining of serial sections with segment-specific biotinylated lectins.

Protein was isolated from whole kidneys by homogenization in RIPA buffer (phosphate buffered saline containing 1% nonidet P-40, 0.5% sodium deoxycholate, 0.1% SDS) with inhibitors (0.1 mg/ml aprotinin, 5 μg/ml leupeptin, 50 μg/ml pepstatin, 1 mM EDTA, 1 mM PMSF and 1:100 v/v phosphatase inhibitor cocktail). Protein content of all samples was determined using the BCA protein assay kit (Pierce, Rockford, Ill.) and equal loading confirmed by Ponseau S solution staining of membranes following transfer.

For Western blotting, 30 kg of total protein lysate was diluted in SDS reducing buffer (62.5 mM Tris-HCL, pH 6.8, 25% v/v glycerol, 2% w/v SDS, 0.01% w/v bromophenol blue, 5% v/v P-mercaptoethanol) and subjected to SDS-PAGE electrophoresis using a 12% separating gel. Samples were transferred to a nitrocellulose membrane, hybridized with blocking buffer (5% dry milk, 0.05% Tween 20), then hybridized with mouse monoclonal anti-TGF-a (Research Diagnostics, Flanders, N.J.). Membranes were washed and hybridized with peroxidase conjugated anti-mouse antibody. Membranes were treated with ECL chemiluminesence reagent (Amersham Pharmacia Biotech, Piscataway, N.J.) and exposed to autoradiography film.

Cyst fluid from day 21 bpk mice was also examined for the presence of TGF-a by immunoprecipitation. 200 μg of total cyst fluid protein was immunoprecipitated with 2 μg of primary antibody (polyclonal anti-TGF-a, Santa Cruz, Calif.), then Protein A/G PLUS-agarose (Santa Cruz) added and the incubation continued. Pellets were collected by centrifugation, washed and resuspended in 1×SDS reducing buffer and boiled for 2-3 minutes.

EXAMPLE 2

Comparison of 1-Acetyl-44(4-But-2-ynyloxy-Benzenesulfonyl)-2,3,4,5-Tetrahydro-1H-[1,4]Benzodiazepine-3-Carboxylic Acid Hydroxyamide Treatment of bpk Mice and 1-Benzyl-4-4-(4-Chloro-Phenoxy)-Benzenesulfonyol]-Piperidine-4-Carboxylic Acid Hydroxamide, (An MMP Inhibitor Without TACE Activity) Treatment of bpk Mice 1-Acetyl-4-(4-But-2-ynyloxy-Benzenesulfonyl)-2,3,4,5-Tetrahydro-1H-[1,4-Benzodiazepine-3-Carboxylic Acid Hydroxyamide Treatment Cystic bpk mice and phenotypically normal littermates were injected with a dose of 100 mg/kg/dose of 1-acetyl-4-(4-but-2-ynyloxy-benzenesulfonyl)-2,3,4,5-tetrahydro-1h-[1,4]benzodiazepine-3-carboxylic acid hydroxyamide given intraperitoneally once daily, in a vehicle containing 0.5% methocellulose (Fluka Biochemica, Ronkonkoma, N.Y.) and 2% Tween 80 (J T Baker, Phillipsburg, N.J.), beginning at postnatal day 7. Age-matched untreated cystic bpk mice and their noncystic littermates served as controls. At day 21, mice were sacrificed. Blood was obtained by orbital puncture prior to sacrifice. Kidney weight and body weight for treated and untreated cystic and noncystic mice were measured at sacrifice. Blood urea nitrogen (BUN) was assessed using a calorimetric assay. Serum creatinine was assessed using standard techniques in the hospital laboratory. Differences in clinical and laboratory parameters between treated and untreated cystic and noncystic mice were analyzed by two-tailed Student's t-test.

Kidneys were fixed in 4% paraformaldehyde and embedded in plastic. Segment-specific localization of cysts was assessed using lectins specific to proximal tubule (*Lotus tetragonolobus*, LTA), and collecting tubule (*Dolichos biflorus* agglutinin, DBA). Serial LTA and DBA stained sections were examined by light microscopy and assessed for severity of cystic dilatations in PTs and CTs, expressed on a scale of 0 to 5 using a modified cystic index:

0=No cysts
1=≦0.11 mm
2=0.12-0.19 mm
3=0.20-0.27 mm
4=0.28-0.35 mm
5=≧0.36 mm

The total number of CT (DBA+/LTA−) cysts and PT (LTA+/DBA−) cysts within a section were counted and expressed as a ratio.

In order to determine if inhibition of secreted TGF-α affected total kidney expression of TGF-α protein, TGF-α expression in 1-acetyl-4-(4-but-2-ynyloxy-benzenesulfonyl)-2,3,4,5tetrahydro-1h-[1,4]benzodiazepine-3-carboxylic acid hydroxyamide-treated and untreated cystic and noncystic animals was assessed by Western analysis as described in Example 1.

Treatment With 1-Benzyl-4-[4-(4-Chloro-Phenoxy)-Benzenesulfonyl]-Piperidine-4-Carboxylic Acid Hydroxamide, an MMP Inhibitor Without TACE Activity Two litters of bpk mice and their noncystic littermates were treated with dosages of 50 mg/kg/day of 1-benzyl-4-[4-(4-chloro-phenoxy)-benzenesulfonyl]-piperidine-4-carboxylic acid hydroxamide given as once daily IP injections. Mice were treated from day 7 of life until day 21, then sacrificed. Analysis of 1-benzyl-4-[4-(4-chloro-phenoxy)-benzenesulfonyl]-piperidine-4-carboxylic acid hydroxamide treated mice included assessment of kidney weight to body weight ratio. The results are listed below in Tables 1, 2, and 3.

TABLE 1

Clinical Parameters of 1-Acetyl-4-(4-But-2-ynyloxy-Benzenesulfonyl)-2,3,4,5-Tetrahydro-1H-[1,4]Benzodiazepine-3-Carboxylic Acid Hydroxyamide Treated and Untreated Mice

| Treatment Group | Kidney Weight (grams) | Body Weight (grams) | Kidney Weight to Body Weight (percent) | BUN (mg/dl) | Creatinine (mg/dl) |
| --- | --- | --- | --- | --- | --- |
| P-21 Cystic (n = 15) | 1.83 +/− 0.6 | 9.3 +/− 2.2 | 19.7 +/− 3.4 | 50 +/− 9[a] | 0.28 +/− 0.13[a] |
| P-21 Cystic + A (n = 6) | 0.93 +/− 0.2** | 8.2 +/− 1.3 | 11.2 +/− 1.3** | 33 +/− 4[b]** | 0.18 +/− 0.05[b] |
| P-21 Noncystic (n = 30) | 0.13 +/− 0.01 | 9.1 +/− 1.0 | 1.5 +/− 0.1 | 19 +/− 4[c] | 0.14 +/− 0.07[e] |
| P-21 Noncystic + A (n = 27) | 0.13 +/− 0.01 | 8.5 +/− 1.0 | 1.5 +/− 0.1 | 17 +/− 4[d] | 0.15 +/− 0.05[e] |

[a]n = 5; [b]n = 4; [c]n = 12; [d]n = 14; [e]n = 10
A = 1-Acetyl-4-(4-But-2-ynyloxy-Benzenesulfonyl)-2,3,4,5-Tetrahydro-1H-[1,4]Benzodiazepine-3-Carboxylic Acid Hydroxyamide
**p < 0.01 cystic treated compared to cystic untreated

TABLE 2

Kidney Histology of 1-Acetyl-4-(4-But-2-ynyloxy-Benzenesulfonyl)-2,3,4,5-Tetrahydro-1H-[1,4]Benzodiazepine-3-Carboxylic Acid Hydroxyamide Treated and Untreated Cystic Mice

| Treatment Group | CT Cystic Index (graded 1–5) | CT Cyst Size Range (mm) | PT Cystic Index (graded 1–5) | PT Cyst Size Range (mm) | Cystic CT/PT Ratio |
| --- | --- | --- | --- | --- | --- |
| Cystic No Treatment | 4.8 +/− 0.4 | 0.012–0.41 | 1.4 +/− 0.5 | 0.012–0.13 | 8 |
| Cystic + A | 3.2 +/− 0.4** | 0.012–0.29 | 1.8 +/− 0.4 | 0.012–0.17 | 1.2** |

A = 1-acetyl-4-(4-but-2-ynyloxy-benzenesulfonyl)-2,3,4,5-tetrahydro-1H-[1,4]benzodiazepine-3-carboxylic acid hydroxyamide
**p < 0.01 cystic treated compared to cystic untreated

TABLE 3

| | \multicolumn{4}{c|}{MMP activity (IC 50) and treatment effect of A versus B} | |
|---|---|---|---|---|---|
| Treatment | MMP-1 | MMP-9 | MMP-13 | TACE | Cystic Kidney Weight to Body Weight (percent) |
| A | 6.6 | 12 | 3 | 8.4 | 11.2 +/− 1.3 |
| B | 801 | 1.1 | 0.9 | 0 | 15.3 +/− 1.7 |
| No Treatment | 0 | 0 | 0 | 0 | 19.7 +/− 3.4 |

A = 1-acetyl-4-(4-but-2-ynyloxy-benzenesulfonyl)-2,3,4,5-tetrahydro-1H-[1,4]benzodiazepine-3-carboxylic acid hydroxyamide
B = 1-Benzyl-4-[4-(4-chloro-phenoxy)-benzenesulfonyl]-piperidine-4-carboxylic acid hydroxamide

What is claimed is:

1. A method for treating and inhibiting the progression of polycystic kidney disease in a mammal in need thereof which comprises providing to said mammal an effective amount of a tumor necrosis factors-alpha converting enzyme (TACE) inhibitor compound wherein the TACE inhibitor compound is a compound of formula II:

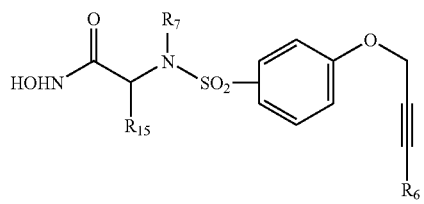

wherein $R_6$ is hydrogen or an optionally substituted substituent selected from phenyl, naphthyl, heteroaryl, alkyl of 1-6 carbon atoms, alkenyl of 2-6 carbon atoms, alkynyl of 2-6 carbon atoms, cycloalkyl of 3-6 carbon atoms or $C_5$-$C_8$-cycloheteroalkyl, $R_7$ is H or alkyl of 1-6 carbon atoms and $R_{15}$ is alkyl of 1-6 carbon atoms or $CH(CH_3)OH$.

2. The method according to claim 1 wherein $R_6$ is methly or substituted methyl; $R_7$ is H or methyl; and $R_{15}$ is isopropyl or $CH(CH_3)OH$.

3. The method according to claim 1 wherein $R_6$ is $CH_3$ or $CH_2OH$; $R_7$ is H or methyl; and $R_{15}$ is isopropyl or $CH(CH_3)OH$.

4. A method for treating and inhibiting the progression of polycystic kidney disease in a mammal in need thereof which comprises providing to said mammal an effective amount of a tumor necrosis factors-alpha converting enzyme (TACE) inhibitor compound wherein the TACE inhibitor compound is a compound of formula III:

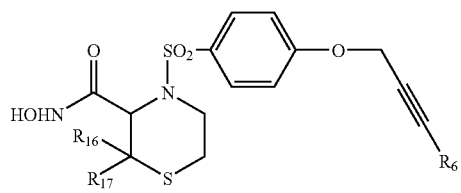

wherein $R_6$ is hydrogen or an optionally substituted substituent selected from phenyl, naphthyl, heteroaryl, alkyl of 1-6 carbon atoms, alkenyl of 2-6 carbon atoms, alkynyl of 2-6 carbon atoms, cycloalkyl of 3-6 carbon atoms or $C_5$-$C_8$-cycloheteroalkyl, and $R_{16}$ and $R_{17}$ are each independently alkyl of 1-6 carbon atoms or $CH_2OH$.

5. The method according to claim 4 wherein $R_6$ is methyl or $CH_2OH$; $R_{16}$ is methyl and $R_{17}$ is methyl.

6. A method for treating and inhibiting the progression of polycystic kidney disease in a mammal in need thereof which comprises providing to said mammal an effective amount of a tumor necrosis factors-alpha converting enzyme (TACE) inhibitor compound wherein the TACE inhibitor compound is selected from the group consisting of 4-(4-but-2-ynyloxy-benzenesulfonyl)-2,2-dimethyl-thiomorpholine-3-carboxylic acid hydroxyamide; (3S)-N-hydroxy-4-({4-[(4-hydroxy-2butynyl)oxy]phenyl}sulfonyl)-2,2-dimethyl-3-thiomorpholinecarboxamide; (2R)-N-hydroxy-2-[({4-[(4-hydroxy-2-butynyl)oxy]phenyl}sulfonyl)(methyl)amino]-3methylbutanamide; and (2R,3S)-2-({[4-(2-butynyloxy)phenyl]sulfonyl}amino)-N,3-dihydroxybutanamide; or a pharmaceutically acceptable salt thereof.

7. A method for treating and inhibiting the progression of polycystic kidney disease in a mammal in need thereof which comprises providing to said mammal an effective amount of a tumor necrosis factors-alpha converting enzyme (TACE) inhibitor compound wherein the TACE inhibitor compound is a compound of formula IV:

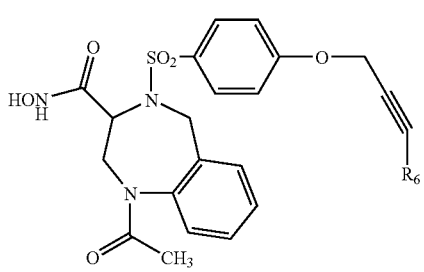

wherein $R_6$ is hydrogen or an optionally substituted substituent selected from phenyl, naphthyl, heteroaryl, alkyl of 1-6 carbon atoms, alkenyl of 2-6 carbon atoms, alkynyl of 2-6 carbon atoms, cycloalkyl of 3-6 carbon atoms or $C_5$-$C_8$-cycloheteroalkyl.

8. The method according to claim 7 wherein $R_6$ is methyl.

9. A method for treating and inhibiting the progression of polycystic kidney disease in a mammal in need thereof which comprises providing to said mammal a combination of an effective amount of a TACE inhibitor compound of claim 1, and an effective amount of an epidermal growth factor receptor kinase inhibitor comprising 4-dimethylamino-but-2-enoic acid [4-(3-chloro-4-fluoro-phenylamino)-3-cyano-7-ethoxy-quinolin-6-yl]-amide.

10. A method for treating and inhibiting the progression of polycystic kidney disease in a mammal in need thereof which comprises providing to said mammal a combination of an effective amount of a TACE inhibitor compound of claim 4, and an effective amount of an epidermal growth factor receptor kinase inhibitor comprising 4-dimethylamino-but-2-enoic acid [4-(3-chloro-4-fluoro-phenylamino)-3-cyano-7-ethoxy-quinolin-6-yl]-amide.

11. A method for treating and inhibiting the progression of polycystic kidney disease in a mammal in need thereof which comprises providing to said mammal a combination of an effective amount of a TACE inhibitor compound of claim 7, and an effective amount of an epidermal growth factor receptor kinase inhibitor comprising 4-dimethylamino-but-2-enoic acid [4-(3-chloro-4-fluoro-phenylamino)-3-cyano-7-ethoxy-quinolin-6-yl]-amide.

* * * * *